(12) United States Patent
Clarke et al.

(10) Patent No.: US 7,109,029 B2
(45) Date of Patent: Sep. 19, 2006

(54) VECTOR CONSTRUCTS

(75) Inventors: Lori Clarke, Olney, MD (US); Mario Gorziglia, Doleystown, PA (US); Paul L. Hallenbeck, Gaithersburg, MD (US); John Leonard Jakubczak, Germantown, MD (US); Michael Kaleko, Rockville, MD (US); Sandrina Phipps, Reston, VA (US)

(73) Assignee: Cell Genesys, Inc., South San Francisco, CA (US)

( * ) Notice: Subject to any disclaimer, the term of this patent is extended or adjusted under 35 U.S.C. 154(b) by 680 days.

(21) Appl. No.: 10/081,961

(22) Filed: Feb. 22, 2002

(65) Prior Publication Data

US 2003/0104624 A1    Jun. 5, 2003

Related U.S. Application Data

(60) Provisional application No. 60/270,885, filed on Feb. 23, 2001.

(51) Int. Cl.
 C12N 15/861 (2006.01)
 C12N 5/10 (2006.01)
 A61K 48/00 (2006.01)

(52) U.S. Cl. .................. 435/325; 435/320.1; 435/455; 435/456; 435/235.1; 435/366; 424/93.1; 424/93.2; 424/93.6; 536/231.1; 536/23.2; 536/23.5; 536/23.72; 536/24.1

(58) Field of Classification Search ............ 435/320.1, 435/455, 456, 457, 235.1, 325, 366; 424/93.1, 424/93.2, 93.6; 536/23.1, 23.2, 23.5, 23.72, 536/24.1
See application file for complete search history.

(56) References Cited

U.S. PATENT DOCUMENTS

| | | | |
|---|---|---|---|
| 5,672,344 A | 9/1997 | Kelley et al. | |
| 5,677,178 A | 10/1997 | McCormick | |
| 5,698,443 A | 12/1997 | Henderson et al. | |
| 5,707,618 A | 1/1998 | Armentano et al. | |
| 5,830,686 A | 11/1998 | Henderson | |
| 5,837,511 A | 11/1998 | Falck-Pedersen et al. | |
| 5,871,726 A | 2/1999 | Henderson et al. | |
| 5,994,128 A | 11/1999 | Fallaux et al. | |
| 5,998,205 A | 12/1999 | Hallenbeck et al. | |
| 6,013,638 A * | 1/2000 | Crystal et al. ................ | 514/44 |
| 6,057,299 A | 5/2000 | Henderson | |
| 6,136,792 A | 10/2000 | Henderson | |
| 6,197,293 B1 | 3/2001 | Henderson et al. | |
| 6,254,862 B1 | 7/2001 | Little et al. | |
| 6,271,207 B1 | 8/2001 | Cristiano et al. | |
| 6,297,219 B1 | 10/2001 | Nabel et al. | |
| 6,420,170 B1 * | 7/2002 | Perricaudet et al. ..... | 435/320.1 |
| 6,432,700 B1 | 8/2002 | Henderson et al. | |
| 6,436,394 B1 | 8/2002 | Henderson et al. | |
| 6,458,586 B1 * | 10/2002 | Tikoo et al. ................ | 435/325 |
| 6,495,130 B1 | 12/2002 | Henderson et al. | |
| 6,686,196 B1 * | 2/2004 | Lieber et al. ............ | 435/320.1 |
| 2001/0006633 A1 | 7/2001 | Kirn | |
| 2001/0046965 A1 * | 11/2001 | Ayares et al. ................. | 514/44 |
| 2004/0241857 A1 * | 12/2004 | Henderson et al. ........ | 424/93.2 |

FOREIGN PATENT DOCUMENTS

| | | |
|---|---|---|
| WO | WO 92/03563 | 3/1992 |
| WO | WO 94/18992 | 9/1994 |
| WO | WO 95/19434 | 7/1995 |
| WO | WO 96/34969 | 11/1996 |
| WO | WO 97/01358 | 1/1997 |
| WO | WO 97/04805 | 2/1997 |
| WO | WO 97/48277 | 12/1997 |
| WO | WO 98/13508 | 4/1998 |
| WO | WO 98/272007 | 6/1998 |
| WO | WO 98/35028 | 8/1998 |
| WO | WO 98/39464 | 9/1998 |
| WO | WO 98/39465 | 9/1998 |
| WO | WO 98/39466 | 9/1998 |
| WO | WO 98/39467 | 9/1998 |
| WO | WO 99/06576 | 2/1999 |
| WO | WO 99/28469 | 6/1999 |
| WO | WO 99/55831 | 11/1999 |
| WO | WO 99/59604 | 11/1999 |
| WO | WO 00/03029 | 1/2000 |
| WO | WO 00/15820 | 3/2000 |
| WO | WO 00/22124 | 4/2000 |
| WO | WO 00/29599 | 5/2000 |
| WO | WO 00/31286 | 6/2000 |
| WO | WO 00/39319 | 6/2000 |
| WO | WO 00/46355 | 8/2000 |
| WO | WO 00/47768 | 8/2000 |
| WO | WO 00/56909 | 9/2000 |
| WO | WO 00/67576 | 11/2000 |
| WO | WO 00/70071 | 11/2000 |

(Continued)

OTHER PUBLICATIONS

U.S. Appl. No. 10/081,969, filed Feb. 22, 2002, Ennist et al.

(Continued)

*Primary Examiner*—David Guzo
(74) *Attorney, Agent, or Firm*—DLA Piper Rudnick Gray Cary US LLP

(57) ABSTRACT

The present invention provides novel viral vectors and methods useful for the minimization of leaky gene expression, and, in particular, of nonspecific transcriptional read-through of genes. Such constructs may be obtained by the insertion of an insulating sequence into a vector construct, such as for example a termination signal sequence upstream of the transcription initiation site of the respective transcription unit.

27 Claims, 10 Drawing Sheets

FOREIGN PATENT DOCUMENTS

| | | |
|---|---|---|
| WO | WO 01/02540 | 1/2001 |
| WO | WO 01/04282 | 1/2001 |
| WO | WO 01/04334 | 1/2001 |
| WO | WO 01/23004 | 4/2001 |
| WO | WO 01/36650 | 5/2001 |
| WO | WO 01/72341 | 10/2001 |
| WO | WO 01/73093 | 10/2001 |
| WO | WO 01/83796 | 11/2001 |
| WO | WO 02/068627 | 9/2002 |

OTHER PUBLICATIONS

Adams, et al., "Transcriptional Control by E2F," Seminars in Cancer Biology, 6:99-108 (1995).

Alemany, et al., "Replicative Adenoviruses for Cancer Therapy," Nature Biotechnology, 18:723-727 (Jul. 2000).

Angelichio, et al., "Comparison of Several Promoters and Polyadenylation Signals for Use in Heterologous Gene Expression in Cultured Drosophila Cells," Nucleic Acids Research, 19(18):5037-5043 (1991).

Armitage, J., "Emerging Applications of Recombinant Human Granulocyte-Macrophage Colony-Stimulating Factor," Blood, 92(12):4491-4508 (Dec. 15, 1998).

Babiss, et al., "Cellular Promoters Incorporated into the Adenovirus Genome: Effects of Viral Regulatory Elements on Transcription Rates and Cell Specificity of Albumin and Beta-Globin Promoters," Molecular and Cellular Biology, 6(11):3798-3806 (Nov. 1986).

Bergsland, et al., "Shedding Old Paradigms: Developing Viruses to Treat Cancer," Journal of Clinical Oncology, 20(9):2220-2222 (May 1, 2002).

Bert, et al., "Generation of an Improved Luciferase Reporter Gene Plasmid that Employs a Novel Mechanism for High-Copy Replication," Plasmid, 44:173-182 (Sep. 2000).

Black, et al., "Regulation of E2F: A Family of Transcription Factors Involved in Proliferation Control," Gene, 237:281-302 (1999).

Bristol, et al., "GM-CSF Containing Oncolytic Adenoviruses for the Treatment of Cancer," Abstract No. P2, presented at The 10th Annual Meeting of the European Society for Gene Therapy. Antibes. France. Oct. 13-16, 2002.

Bristol, et al., "GM-CSF Mediated Stimulation of Innate Anti-tumor Responses," poster presented at the Keystone Symposia, Basic Aspects of Tumor Immunology, Feb. 17-23, 2003.

Bristol, et al., "GM-CSF Containing Oncolytic Adenoviruses for the Treatment of Cancer," poster presented at The 10th Annual Meeting of the European Society for Gene Therapy, Antibes, France, Oct. 13-16, 2002.

Bristol, et al., "In Vivo Anti-Tumor Activity of Oncolytic Adenoviruses that Express GM-CSF in Xenograft Tumor Models," American Society for Gene Therapy, 5th Annual Meeting, Jun. 5-9, 2002; poster presented Jun. 6, 2002.

Bristol, et al., "In Vivo Anti-Tumor Activity of Oncolytic Adenoviruses that Expresses GM-CSF in Xenograft Tumor Models," Molecular Therapy, 5(5):abstract No. 311 (May 2002).

Bruder, et al., "Nuclear Factor Ef-1A Binds to the Adenovirus E1A Core Enhncer Element and to Other Transcriptional Control Regions," Molecular and Cellular Biology, 9(11):5143-5153 (Nov. 1989).

Bryan, et al., "Evidence for an Alternative Mechanism for Maintaining Telomere Length in Human Tumors and Tumor-derived Cell Lines," Nature Medicine, 3(11):1271-1274 (Nov. 1997).

Chang, et al., "Immunogenetic Therapy of Human Melanoma Utilizing Autologous Tumor Cells Transduced to Secrete Granulocyte-Macrophage Colony-Stimulating Factor," Human Gene Therapy, 11:839-850 (Apr. 10, 2000).

Chao, et al., "Assembly of the Cleavage and Polyadenylation Apparatus Requires About 10 Seconds In Vivo and Is Faster for Strong Than for Weak Poly(A) Sites," Molecular and Cellular Biology, 19(8):5588-5600 (Aug. 1999).

Chen, et al., "Antiangiogenic Gene Therapy for Cancer via Systemic Administration of Adenoviral Vectors Expressing Secretable Endostatin," Human Gene Therapy, 11:1983-1996 (Sep. 20, 2000).

Chen, et al., "Cleavage Site Determinants in the Mammalian Polyadenylation Signal," Nucleic Acids Research, 23(14):2614-2620 (1995).

Chia, et al., "A Novel Conditionally Oncolytic Adenovirus for the Treatment of Nasopharyngeal Carcinoma (NPC)," Proceedings of the American Associaton for Cancer Research, 43:1098-1099, abstract No. 5441 (Mar. 2002).

Chiocca, E., "Oncolytic Viruses," Nature, 2:938-950 (Dec. 2002).

Christ, et al., "Modulation of the Inflammatory Properties and Hepatotoxicity of Recombinant Adenovirus Vectors by the Viral E4 Gene Products," Human Gene Therapy, 11:415-427 (Feb. 10, 2000).

Colgan, et al., "Mechanism and Regulation of mRNA Polyadenylation," Genes and Development, 11:2755-2766 (1997).

Curiel, et al., "Strategies to Improve the Therapeutic Utility of Conditionally Replicative Adenoviruses (CRAds) for Cancer Therapy," Proceedings of the American Association for Cancer Research, 43:662, abstract No. 3287 (Mar. 2002).

Demers, et al., "Antitumor Efficacy and Replication of an Oncolytic Adenovirus, 01/PEME, in Tumor Tissue Following Intravenous Administration," Proceedings of the American Association for Caner Research, 43:663, abstract No. 3291 (Mar. 2002).

Denome, et al., "Patterns of Polyadenylation Site Selection in Gene Constructs Containing Multiple Polyadenylation Signals," Molecular and Cellular Biology, 8(11):4829-4839 (Nov. 1988).

DeWeese, et al., "A Phase I Trial of CV706, a Replication-Competent, PSA Selective Oncolytic Adenovirus, for the Treatment of Locally Recurrent Prostate Cancer Following Radiation Therapy," Cancer Research, 61:7464-7472 (Oct. 15, 2001).

Doronin, et al., "Tissue-Specific, Tumor-Selective, Replication-Competent Adenovirus Vector for Cancer Gene Therapy," Journal of Virology, 75(7):3314-3324 (Apr. 2001).

Doronin, et al., "Tumor-Specific, Replication-Competent Adenovirus Vectors Overexpressing the Adenovirus Death Protein," Journal of Virology, 74(13):6147-6155 (Jul. 2000).

Dranoff, et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity," Proc. Natl. Acad. Sci. USA, 90:3539-3543 (Apr. 1993).

Dyson, N., "The Regulation of E2F by pRB-family Proteins," Genes and Development, 12:2245-2262 (Aug. 1998).

Emery, et al., "A Chromatin Insulator Protects Retrovirus Vectors from Chromosomal Position Effects," Proc. Natl. Acad. Sci. USA, 97(16):9150-9155 (Aug. 1, 2000).

Ennist, D., "Oncolytic Adenoviruses Containing GM-CSF for the Treatment of Cancer," oral presentation at the 4th International Conference, The Adjuvant Therapy of Malignant Melanoma, Mar. 15-16, 2002.

Ennist, D., "Oncolytic Adenoviruses Containing GM-CSF for the Treatment of Cancer," abstract presented at the 4th International Conference, The Adjuvant Therapy of Malignant Melanoma, Mar. 15-16, 2002.

Ennist, et al., "Oncolytic Adenoviruses Containing GM-CSF for the Treatment of Cancer," Proceedings of the American Association for Cancer Research, 43:1098, abstract No. 5437 (Mar. 2002).

Ennist, et al., "Oncolytic Adenoviruses Containing GM-CSF for the Treatment of Cancer," oral presentation at the 93rd Annual Meeting of the American Association for Cancer Research, Apr. 6-10, 2002, San Francisco, California.

Fallaux, et al., "New Helper Cells and Matched Early Region 1-Deleted Adenovirus Vectors Prevent Generation of Replication-Competent Adenoviruses," Human Gene Therapy, 9:1909-1917 (Sep. 1, 1998).

Fang, et al., "Diminishing Adenovirus Gene Expression and Viral Replication by Promoter Replacement," Journal of Virology, 71(6):4798-4803 (Jun. 1997).

Fridovic-Keil, et al., "Improved Expression Vectors for Eukaryotic Promoters-Enhancer Studies," BioTechniques, 11(5):572-579 (1991).

Ganly, et al., "A Phase I Study of Onyx-015, an E1B Attenuated Adenovirus, Administered Intratumorally to Patients with Recurrent Head and Neck Cancer," Clinical Cancer Research, 6:798-806 (Mar. 2000).

Gil, et al., "Positon-Dependent Sequence Elements Downstream of AAUAAA Are Required for Efficient Rabbit -Globin mRNA 3' End Formation," Cell, 49:399-406 (May 8, 1987).

Gope, et al., "Abundance and State of Phosphorylation of the Retinoblastoma Susceptibility Gene Product in Human Colon Cancer," Molecular and Cellular Biochemistry, 110:123-133 (1992).

Gu, et al., "Tumor-Specific Transgene Expression from the Human Telomerase Reverse Transcriptase Promoter Enables Targeting of the Therapeutic Effects of the Bax Gene to Cancers," Cancer Research, 60:5359-5364 (Oct. 1, 2000).

Habib, et al., "E1B-Deleted Adenovirus (dl1520) Gene Therapy for Patients with Primary and Secondary Liver Tumors," Human Gene Therapy, 12:219-226 (Feb. 10, 2001).

Hallenbeck, et al., "A Novel Tumor-Specific Replication-Restricted Adenoviral Vector for Gene Therapy of Heptaocellular Carcinoma," Human Gene Therapy, 10:1721-1733 (Jul. 1, 1999).

Hallenbeck, et al., "Oncolytic Adenoviruses Dependent Upon Two Prevalent Alterations in Human Cancer; Disregulation of the RB-Pathway and Telomerase," American Society of Gene Therapy 5th Annual Meeting, Jun. 5-9, 2002, poster presented on Jun. 5, 2002.

Hallenbeck, et al., "Oncolytic Adenoviruses Dependent Upon Two Prevalent Alterations in Human Cancer; Disregulation of the RB-Pathway and Telomerase," Molecular Therapy, 5(5):Abstract 165 (May 2002).

Hallenbeck, P., "Oncolytic Adenoviruses Dependent Upon Two Prevalent Alterations in Human Cancer; Disregulation of the Rb-Pathway and Telomerase," oral presentation presented at the 3rd International Symposium on Genetic Anticancer Agents, Amsterdam, The Netherlands, Mar. 1-2, 2002.

Hans, et al., "Functionally Significant Secondary Structure of the Simian Virus 40 Late Polyadenylation Signal," Molecular and Cellular Biology, 20(8):2926-2932 (Apr. 2000).

Hatfield, et al., "Redundant Elements in the Adenovirus Type 5 Inverted Terminal Repeat Promote Bidirectional Transcription In Vitro and Are Important for Virus Growth In Vivo," Virology, 184:265-276 (1991).

Hatfield, et al., "The NFIII/OCT-1 Binding Site Stimulates Adenovirus DNA Replication In Vivo and Is Functionally Redundant with Adjacent Sequences," Journal of Virology, 67(7):3931-3939 (Jul. 1993).

Hay, C., "Oncolytic Adenvovirus Dependent Upon Two Prevalent Alterations in Human Cancer," The 10th Annual Meeting of the European Society of Gene Therapy, Antibes, France, Oct. 13-16, 2002, oral presentation presented on Oct. 16, 2002.

Hearing, et al., "The Adenovirus Type 5 E1A Transcriptional Control Region Contains a Duplicated Enhancer Element," Cell, 33:695-703 (1983).

Heise, et al., "Efficacy of a Replication-Competent Adenovirus (ONYX-015) Following Intratumoral Injection: Intratumoral Spread and Distribution Effects," Cancer Gene Therapy, 6(6):499-504 (1999).

Heise, et al., "Replication-Selective Adenoviruses as Oncolytic Agents," The Journal of Clinical Investigaton, 105(7):847-851 (Apr. 2000).

Herminston, T., "Gene Delivery From Replication-Selective Viruses: Arming Guided Missiles in the War Against Cancer," The Journal of Clinical Investigation, 105(9):1169-1172 (May 2000).

Hiyama, et al., "Telomerase Activity in Small-Cell and Non-Small-Cell Lung Cancers," Journal of the National Cancer Institute, 87(12):895-902 (Jun. 21, 1995).

Horikawa, et al., "Cloning and Characterization of the Promoter Region of Human Telomerase Reverse Transcriptase Gene," Cancer Researh, 59:826-830 (Feb. 15, 1999).

Hurford, et al., "pRB and p107/p130 are Required for the Regulated Expression of Different Sets of E2F Responsive Genes," Genes & Development, 11:1447-1463 (1997).

Hwang, et al., "Polyadenylation of Vesicular Stomatitis Virus mRNA Dictates Efficient Transcription Termination at the Intercistronic Gene Junctions," Journal of Virology, 72(3):1805-1813 (Mar. 1998).

International Search Report for PCT/US02/05280, Feb. 14, 2003.

Jaffee, et al., "Novel Allogeneic Granulocyte-Macrophage Colony-Stimulating Factor-Secreting Tumor Vaccine for Pancreatic Cancer: A Phase I Trial of Safety and Immune Activation," Journal of Clinical Oncology, 19(1):145-156 (Jan. 1, 2001).

Jakubczak, et al., "Construction and Characterization of Oncolytic Adenoviruses," Molecular Therapy, 3(5):Abstract 442 (May 2001).

Jakubczak, et al., "Construction and Characterization of Oncolytic Adenoviruses," The Fourth Annual Meeting of the American Society of Gene Therapy, May 30-Jun. 3, 2001; poster presented on Jun. 1, 2001.

Jakubczak, et al., "Evaluation of In Vivo Selectivity of Oncolytic Adenoviruses Following Intravenous Administration in SCID Mice Using Toxicological and Molecular Parameters," American Society of Gene Therapy, 5th Annual Meeting, Jun. 5-9, 2002; poster presented Jun. 7, 2002.

Jakubczak, et al., "Evaluation of In Vivo Selectivity of Oncolytic Adenoviruses Following Intravenous Administration in SCID Mice Using Toxicological and Molecular Parameters," Molecular Therapy, 5(5):abstract No. 851 (Mar. 2002).

Jakubczak, J., "An Oncolytic Adenovirus Dependent Upon Two Prevalent Alterations in Human Cancer; Disregulation of the Rb-Pathway and Telomerase," oral presentation presented at the US-Japan Cooperative Cancer Research Program, Telomeres and Telomerase in Cancer Research, Maui, HI, Aug. 3-5, 2002.

Johnson, et al., "Autoregulatory Control of E2F1 Expression in Response to Positive and Negative Regulators of Cell Cycle Progression," Genes and Development, 8:1514-1525 (1994).

Johnson, et al., "Cytosine Deaminase-armed Selectively Replicating Adenovirus for the Treatment of Cancer," Proceedings of the American Association for Cancer Research, 43:656, abstract No. 3257 (Mar. 2002).

Johnson, et al., "Selectively Replicating Adenoviruses Targeting Deregulated E2F Activity are Potent, Systemic Antitumor Agents," Cancer Cell, 1:325-337 (May 2002).

Kaelin, et al., "Expression Cloning of a cDNA Encoding a Retinoblastoma-Binding Protein with E2F-like Properties," Cell, 70:351-364 (Jul. 24, 1992).

Kessler, et al., "Requirement of A-A-U-A-A-A and Adjacent Downstream Sequences for SV40 Early Polyadenylation," Nucleic Acids Research, 14(12):4939-4953 (1986).

Kilian, et al., "Isolation of a Candidate Human Telomerase Catalytic Subunit Gene, Which Reveals Complex Splicing Patterns in Different Cell Types," Human Molecular Genetics, 6(12):2011-2019 (1997).

Kim, et al., "Specific Association of Human Telomerase Activity with Immortal Cells and Cancer," Science, 266:2011-2015 (Dec. 23, 1994).

Kirn, D., "Clinical Research Results with dl1520 (Onyx-015), a Replication-selective Adenovirus for the Treatment of Cancer: What Have We Learned?" Gene Therapy, 8:89-98 (Jan. 2001).

Kirn, D., "Replication-selective Microbiological Agents: Fighting Cancer With Targeted Germ Warfare," The Journal of Clinical Investigation, 105(7):837-839 (Apr. 2000).

Kirn, D., "Replication-selective Oncolytic Adenoviruses: Virotherapy Aimed at Genetic Targets in Cancer," Oncogene, 19:6660-6669 (Dec. 27, 2000).

Kirn, D., "Virotherapy for Cancer: Current Status, Hurdles, and Future Directions," Cancer Gene Therapy, 9:959-960 (Dec. 2002).

Kirn, et al., "ONYX-015: Clinical Data are Encouraging," Nature Medicine, 4(12):1341-1342 (Dec. 1998).

Kirschweger, G., "Genetic Therapies, Inc.: Tight-Lipped for Now," Molecular Therapy, 7(3):293 (Mar. 2003).

Kiyono, et al., "Both Rb/p16INKa Inactivation and Telomerase Activity are Required to Immortalize Human Epithelial Cells," Nature, 396:84-88 (Nov. 5, 1998).

Kovesdi, et al., "Identification of a Cellular Transcription Factor Involved in E1A Trans-Activation," Cell, 45:219-228 (Apr. 25, 1986).

Kurihara, et al., "Selectivity of a Replication-Competent Adenovirus for Human Breast Carcinoma Cells Expressing the MUC1 Antigen," The Journal of Clinical Investigation, 106(6);763-771 (Sep. 2000).

Kwong, et al., "Combination Therapy with Suicide and Cytokine Genes for Hepatic Metastases of Lung Cancer," Chest, 112(5):1332-1337 (Nov. 1997).

La Thangue, N., "DRTF1/E2F: An Expanding Family of Heterodimeric Transcription Factors Implicated in Cell-Cycle Control," Trends in Biochemical Science, 19:108-114 (Mar. 1994).

Li, et al., "A Hepatocellular Carcinoma-specific Adenovirus Variant, CV890, Eliminates Distant Human Liver Tumors in Combination with Doxorubicin," Cancer Research, 61:6428-6436 (Sep. 1, 2001).

Li, et al., "Replication Competent Oncolytic Adenovirus for Colon Cancer Therapy," Proceedings of the American Association for Cancer Research, 43;858, abstract No. 4251 (Mar. 2002).

Limbach, et al., "Development of Adenovirus Serotype 35 as a Gene Transfer Vector," poster presented at The 10th Annual Meeting of the European Society for Gene Therapy, Antibes, France, Oct. 13-16, 2002.

Liu, et al., "Optimised Oncolytic Herpes Simplex Virus for Cancer Treatment," Abstract No. Or33, presented at The 10th Annual Meeting of the European Society for Gene Therapy, Antibes, France, Oct. 13-16, 2002.

Liu, et al., "Optimized Oncolytic Herpes Simplex Virus for Cancer Treatment," poster presented at the 10th Annual Meeting of the European Society for Gene Therapy, Antibes, France, Oct. 13-16, 2002.

Lorence, et al., "Systemic Therapy of Human Tumor Xenografts Using PV701, an Oncolytic Strain of Newcastle Disease Virus, in Combination with a Cytotoxic Drug Demonstrates at Least Additive Antitumor Responses," Proceedings of the American Association for Cancer Research, 43:1096, abstract No. 5428 (Mar. 2002).

Lyons, R., "Multiple Approaches to Treating Systemic Disease with Oncolytic Adenoviruses," ASM Gene Therapy Conference, Feb. 28, 2003, Banff, Alberta CA; oral presentation presented Feb. 28, 2003.

Mabjeesh, et al., "Gene Therapy of Prostate Cancer: Current and Future Directions," Endocrine-Related Cancer, 9:115-139 (Jun. 2002).

McDevitt, et al., "Sequences Capable of Restoring poly(A) Site Function Define Two Distinct Downstream Elements," The EMBO Journal, 5(11):2907-2913 (1986).

Medina, et al., "Adenovirus-Mediated Cytotoxicity of Chronic Lymphocytic Leukemia Cells," Blood, 94(10):3499-3508 (Nov. 15, 1999).

Morris, et al., "Therapy of Head and Neck Squamous Cells Carcinoma with an Oncolytic Adenovirus Expressing HSV-tk," Molecular Therapy, 1(1):56-62 (Jan. 2000).

Nemunaitis, et al., "Selective Replication and Oncolysis in p53 Mutant Tumors with ONYX-015, an E1B-55kD Gene-Deleted Adenovirus, in Patients with Advanced Head and Neck Cancer: A Phase II Trial," Cancer Research, 60:6359-6366 (Nov. 15, 2000).

Neuman, et al., "Structure and Partial Genomic Sequence of the Human E2F1 Gene," Gene, 173:163-169 (1996).

Neuman, et al., "Transcription of the E2F-1 Gene is Rendered Cell Cycle Dependent by E2F DNA-Binding Sites Within its Promoter," Molecular and Cellular Biology, 14(10):6607-6615 (Oct. 1994).

Oh, et al., "In Vivo and In Vitro Analyses of Myc for Differential Promoter Activities of the Human Telomerase (hTERT) Gene in Normal and Tumor Cells," Biochemical and Biophysical Research Communications, 263:361-365 (1999).

Paielli, et al., "Evaluation of the Biodistribution, Persistence, Toxicity, and Potential of Germ-Line Transmission of a Replication-Competent Human Adenovirus Following Intraprostatic Administration in the Mouse," Molecular Therapy, 1(3):263-274 (Mar. 2000).

Pardoll, D., "Paracrine Cytokine Adjuvants in Cancer Immunotherapy," Annu. Rev. Immunol., 13:399-415 (1995).

Parr, et al., "Tumor-selective Transgene Expression In Vivo Mediated by an E2F-responsive Adenoviral Vector," Nature Medicine, 3(10):1145-1149 (Oct. 1997).

Pecora, et al., "Phase I Trial of Intravenous Administration of PV701, an Oncolytic Virus, in Patients With Advanced Solid Cancers," Journal of Clinical Oncology, 20(9):2251-2266 (May 1, 2002).

Peter, et al., "A Novel Attenuated Replication-Competent Adenovirus for Melanoma Therapy," Abstract No. P78, presented at The 10th Annual Meeting of the European Society for Gene Therapy, Antibes, France, Oct. 13-16, 2002.

Poole, et al., "Activity, Function, and Gene Regulation of the Catalytic Subunit of Telomerase (hTERT)," Gene, 269:1-12 (May 2001).

Porosnicu, et al., "Increased Efficiency of the Selectively Oncolytic Vesicular Stomatitis Virus by Genetic Manipulation with Expression of Suicide Genes," Proceedings of the American Association foir Cancer Research, 43:1096-1097, abstract No. 5431 (Mar. 2002).

Powell, et al., "A Conditionally Replicative Adenovirus Driven by the Human Telomerase Promoter Provides Broad-Spectrum Anti-Tumor Activity," Molecular Therapy, 5(5):abstract No. 51 (May 2002).

Prell, et al., "Tumor Necrosis Factor (-armed Defective p53-pathway Selective Replicating Adenovirus for Cancer Treatment," Proceedings of the American Association for Cancer Research, 43:1110, abstract No. 5500 (Mar. 2002).

Ramachandra, et al., "Re-engineering Adenovirus Regulatory Pathways to Enhance Oncolytic Specificity and Efficacy," Nature Biotechnology, 19:1035-1041 (Nov. 2001).

Raschke, et al., "A Replication Competent Dual-ad Vector for Treatment of Prostate Cancer," Abstract No. Or41, presented at The 10th Annual Meeting of the European Society for Gene Therapy, Antibes, France, Oct. 13-16, 2002.

Rassa, et al., "Molecular Basis for Naturally Occuring Elevated Readthrough Transcription Across the M-F Junction of the Paramyxovirus SV5," Virology, 247:274-286 (1998).

Reddy, et al., "Development of Adenovirus Serotype 35 as a Gene Transfer Vector," American Society of Gene Therapy 5th Annual Meeting, Jun. 5-9, 2002, poster presented Jun. 6, 2002.

Reddy, et al., "Development of Adenovirus Serotype 35 as Gene Transfer Vector," American Society of Gene Therapy 5th Annual Meeting, Jun. 5-9, 2002, Molecular Therapy, 5(5):S67-S68, abstract No. 200.

Reszka, et al., "New Targeting System for High-efficient Delivery of Anti-neoplastic Drugs or Genes into the Angiogenetic Areas of Liver Tumors," Proceedings of the American Association for Cancer Research, 43:663, abstract No. 3289 (Mar. 2002).

Ries, et al., "ONYX-015: Mechanisms of Action and Clinical Potential of a Replication-Selective Adenovirus," British Journal of Cancer, 86:5-11 (Jan. 7, 2002).

Rodriguez, et al., "Prostate Attenuated Replication Competent Adenovirus (ARCA) CN706: A Selective Cytotoxic for Prostate-specific Antigen-positive Prostate Cancer Cells," Cancer Research, 57:2559-2563 (Jul. 1, 1997).

Russell, W., "Update on Adenovirus and Its Vectors," Journal of General Virology, 81:2573-2604 (Nov. 2000).

Ryan, et al., "An Oncolytic Adenovirus Dependent on Two Prevalent Alterations in Human Cancer: Efficacy, Tolerability, and Tumor-Selectivity Following Systemic Administration," Eleventh International Conference on Gene Therapy of Cancer, San Diego, CA, Dec. 12-14, 2002, 10(Suppl. 1):abstract No. 036.

Ryan, et al., "Anti-Tumor Efficacy and Preclinical Proof-of-Concept Following Systemic Administration of an Oncolytic Adenovirus Dependent Upon Two Prevalent Alterations in Human Cancer," Abstract No. Or34, presented at The 10th Annual Meeting of the European Society for Gene Therapy, Antibes, France, Oct. 13-16, 2002.

Sanchez-Prieto, et al., "Lack of Correlation Between p53 Protein Level and Sensitivity to DNA-damaging Agents in Keratinocytes Carrying Adenovirus E1a Mutants," Oncogene, 11:675-682 (1995).

Sauthoff, et al., "Deletion of the Adenoviral E1b-19kD Gene Enhances Tumor Cell Killing of a Replicating Adenoviral Vector," Human Gene Therapy, 11:379-388 (Feb. 10, 2000).

Sauthoff, et al., "p53 Expression Late in the Life Cycle of a Replication-competent Adenovirus Improves Tumor Cell Killing and Deletion of the Death Protein Improves Specificity," Proceedings of the American Association for Cancer Research, 43:1098, abstract No. 5439 (Mar. 2002).

Schwarz, et al., "Interactions of the p107 and Rb Proteins with E2F During the Cell Proliferation Response," The EMBO Journal, 12(3):1013-1020 (1993).

Sellers, et al., "A Potent Transrepression Domain in the Retinoblastoma Protein Induces a Cell Cycle Arrest When Bound to E2F Sites," Proc. Natl. Acad. Sci. USA, 92:11544-11548 (Dec. 1995).

Shay, et al., "A Survey of Telomerase Activity in Human Cancer," European Journal of Cancer, 33(5):787-791 (1997).

Shay, et al., "Telomerase and Cancer," Human Molecular Genetics, 10(7):677-685 (Apr. 2001).

Shi, et al., "Modulation of the Specificity and Activity of a Cellular Promoter in an Adenoviral Vector," Human Gene Therapy, 8:403-410 (Mar. 1, 1997).

Steinwaeder, et al., "Insulation from Viral Transcriptional Regulatory Elements Improves Inducible Transgene Expression from Adenovirus Vectors In Vitro and In Vivo," Gene Therapy, 7(7):556-567 (Apr. 2000).

Stewart, D., "Oncolytic Adenovirus Dependent on Two Prevalent Alterations in Human Cancer," oral presentation presented at the Eleventh International Conference on Gene Therapy of Cancer, San Diego, CA, Dec. 12-14, 2002.

Stewart, et al., "OAV001, an Oncolytic Adenovirus Dependent on Rb-Pathway Alterations in Human Cancer," American Society for Gene Therapy, 5th Annual Meeting, Jun. 5-9, 2002; oral presentation presented Jun. 7, 2002.

Stewart, et al., "OAV001, an Oncolytic Adenovirus Dependent on Rb-Pathway Alterations in Human Cancer," Molecular Therapy, 5(5):abstract No. 53 (May 2002).

Stewart, et al., "Telomerase and Human Tumorigenesis," Seminars in Cancer Biology, 10:399-406 (Dec. 2000).

Strauss, et al., "Unrestricted Cell Cycling and Cancer," Nature Medicine, 1(12):1245-1246 (Dec. 1995).

Takahashi, et al., "Analysis of Promoter Binding by the E2F and pRB Families In Vivo: Distinct E2F Proteins Mediate Activation and Repression," Genes & Development, 14:804-816 (Apr. 1, 2000).

Takakura, et al., "Cloning of Human Telomerase Catalytic Subunit (hTERT) Gene Promoter and Identification of Proximal Core Promoter Sequences Essential for Transcriptional Activation in Immortalized and Cancer Cells," Cancer Research, 59:551-557 (Feb. 1, 1999).

Terhune, et al., "Regulation of Human Papillomavirus Type 31 Polyadenylation During the Differentiation-Dependent Life Cycle," Journal of Virology, 73(9):7185-7192 (Sep. 1999).

Tevosian, et al., "Expression of the E2F-1/DP-1 Transcription Factor in Murine Development," Cell Growth and Differentiation, 7:43-52 (Jan. 1996).

Tollefson, et al., "The Adenovirus Death Protein (E3-11.6K) Is Requried at Very Late Stages of Infection for Efficient Cell Lysis and Release of Adenovirus from Infected Cells," Journal of Virology, 70(4):2296-2306 (Apr. 1996).

Tsukuda, et al., "An E2F-responsive Replication-selective Adenovirus Targeted to the Defective Cell Cycle in Cancer Cells: Potent Antitumoral Efficacy but No Toxicity to Normal Cells," Cancer Research, 62:3438-3447 (Jun. 15, 2002).

Vassaux, et al., "Insulation of a Conditionally Expressed Transgene in an Adenoviral Vector," Gene Therapy, 6:1192-1197 (1999).

Vile, et al., "The Oncolytic Virotherapy Treatment Platform for Cancer: Unique Biological and Biosafety Points to Consider," Cancer Gene Therapy, 9:1062-1067 (Dec. 2002).

Waehler, et al., "Experimental Gene Therapy of Hepatocellular Carcinoma: Expression of IL-12, 4-1BBL and IL-2 From a Single Adenoviral Vector," Abstract No. P33, presented at The 10th Annual Meeting of the European Society for Gene Therapy, Anitbes, France, Oct. 13-16, 2002.

Wahle, et al., "The Mechanism of 3' Cleavage and Polyadenylation of Eukrayotic Pre-MmA," Progress in Nucleic Acid Research and Molecular Biology, 57:41-71 (1997).

Weinberg, R., "The Retinoblastoma Protein and Cell Cycle Control," Cell, 81:323-330 (May 5, 1995).

Wen, et al., "Effect of Viral Replication on Pharmacokinetics of 01/PEME, a Recombinant Oncolytic Adenovirus, in a Human Lung Cancer Xenograft Model," Proceedings of the American Association for Cancer Research, 43:1098, abstract No. 5440 (Mar. 2002).

Wold, et al., "Adenovirus Proteins that Subvert Host Defenses," Trends in Microbiology, 2(11):437-443 (Nov. 1994).

Wold, et al., "Immune Responses to Adenoviruses: Viral Evasion Mechanisms and Their Implications for the Clinic," Current Opinion in Immunology, 11:380-386 (1999).

Yu, et al., "Identification of the Transcriptional Regulatory Sequences of Human Kallikrein 2 and Their Use in the Construction of Calydon Virus 764, an Attenuated Replication Competent Adenovirus for Prostate Cancer Therapy," Cancer Research, 59:1498-1504 (Apr. 1, 1999).

Yu, et al., "The Addition of Adenovirus Type 5 Region E3 Enables Calydon Virus 787 to Eliminate Distant Prostate Tumor Xenografts," Cancer Research, 59:4200-4203 (Sep. 1, 1999).

Zhou, et al., "E1A Sensitizes HER2/neu-overexpressing Ewing's Sarcoma Cells to Topoisomerase II-targeting Anticancer Drugs," Cancer Research, 61:3394-3398 (Apr. 15, 2001).

Zhu, et al., "In Vivo Spread of Oncolytic Adenoviruses in Xenograft Tumor Models," Molecular Therapy, 5(5):abstract No. 317 (May 2002).

Zsengeller, et al., "Adenovirus-Mediated Granulocyte-Macrophage Colony-Stimulating Factor Improves Lung Pathology of Pulmonary Alveolar Proteinosis in Granulocyte-Macrophage Colony-Stimulating Factor-Deficient Mice," Human Gene Therapy, 9:2101-2109 (Sep. 20, 1998).

Zwicker, et al., "Cell Cycle-regulated Transcription in Mammalian Cells," Progress in Cell Cycle Research, 1:91-99 (1995).

Dong, et al., "Angiostatin-Mediated Suppression of Cancer Metastases by Primary Neoplasms Engineered to Produce Granulocyte/Macrophage Colony-Stimulating Factor," J. Exp. Med., 188(4):755-763 (Aug. 17, 1998).

* cited by examiner

A. CTTATCGATACCGTCGAAACTTGTTTATTGCAGCTTATAATGGTTACAAATAAAGCAATAGCAT

CACAAATTTCACAAATAAAGCATTTTTTTCACTGCATTCTAGTTGTGGTTTGTCCAAACTCATCA
             +++++                          ↑              ++++ ++++++

ATGTATCTTATCATGTC            CLEAVAGE SITE

B. ■━━━━━━━━━━━━━━━GCA

C. ■━━━━━━━━━━━━━━━GCAaaaaaaaaaaaaaaaaaaaaaa

+ UPSTREAM AND DOWNSTREAM
  CLEAVAGE-POLYADENYLATION ELEMENTS

```
  1 CATCATCAATAATATACCTTATTTTGGATTGAAGCCAATATGATAATGAGGGGGTGGAGT
    +--------------------------ITR------------------------------

61 TTGTGACGTGGCGCGGGGCGTGGGAACGGGGCGGGTGACGTAGGGCGCGATCAAGCTTAT
    +--------------------------ITR-----------+               +----

121 CGATACCGTCGAAACTTGTTTATTGCAGCTTATAATGGTTACAAATAAAGCAATAGCATC
    --------------------------polyA-----------------------------

181 ACAAATTTCACAAATAAAGCATTTTTTTCACTGCATTCTAGTTGTGGTTTGTCCAAACTC
    --------------------------polyA-----------------------------

241 ATCAATGTATCTTATCATGTCTGGATCCGCGCCGCTAGCGATCATCCGGACAAAGCCTGC
    -------------------+                      +-----------------

301 GCGCGCCCCGCCCCGCCATTGGCCGTACCGCCCCGCGCCGCCGCCCCATCTCGCCCCTCG
    -----------------------E2F-1 PROMOTER----------------------

361 CCGCCGGGTCCGGCGCGTTAAAGCCAATAGGAACCGCCGCCGTTGTTCCCGTCACGGCCG
    -----------------------E2F-1 PROMOTER----------------------

421 GGGCAGCCAATTGTGGCGGCGCTCGGCGGCTCGTGGCTCTTTCGCGGCAAAAAGGATTTG
    -----------------------E2f-1 PROMOTER----------------------

481 GCGCGTAAAAGTGGCCGGGACTTTGCAGGCAGCGGCGGCCGGGGGCGGAGCGGGATCGAG
    -----------------------E2f-1 PROMOTER----------------------

541 CCCTCGATGATATCAGATCATCGGATCCCGGTCGACTGAAAATGAGACATATTATCTGCC
    --------------+                       +---------------------

601 ACGGAGGTGTTATTACCGAAGAAATGGCCGCCAGTCTTTTGGACCAGCTGATCGAAGAGG
    ------------------------E1a GENE---------------------------

661 TACTGGCTGATAATCTTCCACCTCCTAGCCATTTTGAACCACCTACCCTTCACGAACTGT
    ------------------------E1a GENE---------------------------

721 ATGATTTAGACGTGACGGCCCCCGAAGATCCCAACGAGGAGGCGGTTTCGCAGATTTTTC
    ------------------------E1a GENE---------------------------

781 CCGACTCTGTAATGTTGGCGGTGCAGGAAGGGATTGACTTACTCACTTTTCCGCCGGCGC
    ------------------------E1a GENE---------------------------

841 CCGGTTCTCCGGAGCCGCCTCACCTTTCCCGGCAGCCCGAGCAGCCGGAGCAGAGAGCCT
    ------------------------E1a GENE---------------------------
```

Fig. 3A

```
 901 TGGGTCCGGTTTCTATGCCAAACCTTGTACCGGAGGTGATCGATCTTACCTGCCACGAGG
     -----------------------E1a GENE---------------------------

961 CTGGCTTTCCACCCAGTGACGACGAGGATGAAGAGGGTGAGGAGTTTGTGTTAGATTATG
     -----------------------E1a GENE---------------------------

1021 TGGAGCACCCCGGGCACGGTTGCAGGTCTTGTCATTATCACCGGAGGAATACGGGGGACC
     -----------------------E1a GENE---------------------------

1081 CAGATATTATGTGTTCGCTTTGCTATATGAGGACCTGTGGCATGTTTGTCTACAGTAAGT
     -----------------------E1a GENE---------------------------

1141 GAAAATTATGGGCAGTGGGTGATAGAGTGGTGGGTTTGGTGTGGTAATTTTTTTTTTAAT
     -----------------------E1a GENE---------------------------

1201 TTTTACAGTTTTGTGGTTTAAAGAATTTTGTATTGTGATTTTTTTAAAAGGTCCTGTGTC
     -----------------------E1a GENE---------------------------

1261 TGAACCTGAGCCTGAGCCCGAGCCAGAACCGGAGCCTGCAAGACCTACCCGCCGTCCTAA
     -----------------------E1a GENE---------------------------

1321 AATGGCGCCTGCTATCCTGAGACGCCCGACATCACCTGTGTCTAGAGAATGCAATAGTAG
     -----------------------E1a GENE---------------------------

1381 TACGGATAGCTGTGACTCCGGTCCTTCTAACACACCTCCTGAGATACACCCGGTGGTCCC
     -----------------------E1a GENE---------------------------

1441 GCTGTGCCCCATTAAACCAGTTGCCGTGAGAGTTGGTGGGCGTCGCCAGGCTGTGGAATG
     -----------------------E1a GENE---------------------------

1501 TATCGAGGACTTGCTTAACGAGCCTGGGCAACCTTTGGACTTGAGCTGTAAACGCCCCAG
     -----------------------E1a GENE---------------------------

1561 GCCATAAGGTGTAAACCTGTGATTGCGTGTGTGGTTAACGCCTTTGTTTGCTGAATGAGT
     -----------------------E1a GENE---------------------------

1621 TGATGTAAGTTTAATAAAGGGTGAGATAATGTTTAACTTGCATGGCGTGTTAAATGGGGC
     --------------------------+-------------------------------

1681 GGGGCTTAAAGGGTATATAATGCGCCGTGGGCTAATCTTGGTTACATCTGACCTCATGGA
     -----------------------E1b GENE---------------------------

1741 GGCTTGGGAGTGTTTGGAAGATTTTTCTGCTGTGCGTAACTTGCTGGAACAGAGCTCTAA
     -----------------------E1b GENE---------------------------

33881 AACCTACGCCCAGAAACGAAAGCCAAAAAACCCACAACTTCCTCAAATCGTCACTTCCGT

33941 TTTCCCACGTTACGTCACTTCCCATTTTAATTAAGAATTCTACAATTCCCAACACATACA

34001 AGTTACTCCGCCCTAAAACCCTGGGCGAGTCTCCACGTAAACGGTCAAAGTCCCCGCGGC
                              +-PACKAGING SIGNAL---------------------
34061 CCTAGACAAATATTACGCGCTATGAGTAACACAAAATTATTCAGATTTCACTTCCTCTTA
      ---------------------PACKAGING SIGNAL---------------------
34121 TTCAGTTTTCCCGCGAAAATGGCCAAATCTTACTCGGTTACGCCCAAATTTACTACAACA
      ---------------------PACKAGING SIGNAL---------------------
34181 TCCGCCTAAAACCGCGCGAAAATTGTCACTTCCTGTGTACACCGGCGCACACCAAAAACG
      ----------------------------------+

34241 TCACTTTTGCCACATCCGTCGCTTACATGTGTTCCGCCACACTTGCAACATCACACTTCC

34301 GCCACACTACTACGTCACCCGCCCCGTTCCCACGCCCCGCGCCACGTCACAAACTCCACC
                      +----------------ITR---------------------
34361 CCCTCATTATCATATTGGCTTCAATCCAAAATAAGGTATATTATTGATGATG
      ---------------------------ITR---------------------+

Fig. 3C

```
  1 CATCATCAATAATATACCTTATTTTGGATTGAAGCCAATATGATAATGAGGGGGTGGAGT
    ------------------------------- ITR --------------------------
 61 TTGTGACGTGGCGCGGGGCGTGGGAACGGGGCGGGTGACGTAGGGCGCGCCGCTAGCGAT
    --------------------------- ITR -------------++---- MCS --------
121 ATCGGATCCCGGTCGACTGAAAATGAGACATATTATCTGCCACGGAGGTGTTATTACCGA
    ------------------------------E1a----------------------------
181 AGAAATGGCCGCCAGTCTTTTGGACCAGCTGATCGAAGAGGTACTGGCTGATAATCTTCC
    ------------------------------E1a----------------------------
241 ACCTCCTAGCCATTTTGAACCACCTACCCTTCACGAACTGTATGATTTAGACGTGACGGC
    ------------------------------E1a----------------------------
301 CCCCGAAGATCCCAACGAGGAGGCGGTTTCGCAGATTTTTCCCGACTCTGTAATGTTGGC
    ------------------------------E1a----------------------------
361 GGTGCAGGAAGGGATTGACTTACTCACTTTTCCGCCGGCGCCCGGTTCTCCGGAGCCGCC
    ------------------------------E1a----------------------------
421 TCACCTTTCCCGGCAGCCCGAGCAGCCGGAGCAGAGAGCCTTGGGTCCGGTTTCTATGCC
    ------------------------------ E1a ---------------------------
481 AAACCTTGTACCGGAGGTGATCGATCTTACCTGCCACGAGGCTGGCTTTCCACCCAGTGA
    ------------------------- E1a ---------------------------------
541 CGACGAGGATGAAGAGGGTGAGGAGTTTGTGTTAGATTATGTGGAGCACCCCGGGCACGG
    --------------------------- E1a ---------------------------
601 TTGCAGGTCTTGTCATTATCACCGGAGGAATACGGGGGACCCAGATATTATGTGTTCGCT
    ------------------------- E1a ---------------------------
```

Fig. 4

```
  1 CATCATCAATAATATACCTTATTTTGGATTGAAGCCAATATGATAATGAGGGGGTGGAGT
    +------------------------ITR---------------------------------

61 TTGTGACGTGGCGCGGGGCGTGGGAACGGGGCGGGTGACGTAGGGCGCGATCAAGCTTAT
    ------------------------ITR---------------+          +----

121 CGATACCGTCGAAACTTGTTTATTGCAGCTTATAATGGTTACAAATAAAGCAATAGCATC
    --------------------------polyA--------------------------

181 ACAAATTTCACAAATAAAGCATTTTTTTCACTGCATTCTAGTTGTGGTTTGTCCAAACTC
    --------------------------polyA--------------------------

241 ATCAATGTATCTTATCATGTCTGGATCCGCGCCGCTAGCGATATCGGATCCCGGTCGACT
    --------------------+                                    +--

301 GAAAATGAGACATATTATCTGCCACGGAGGTGTTATTACCGAAGAAATGGCCGCCAGTCT
    -----------------------------E1a----------------------------

361 TTTGGACCAGCTGATCGAAGAGGTACTGGCTGATAATCTTCCACCTCCTAGCCATTTTGA
    -----------------------------E1a----------------------------

421 ACCACCTACCCTTCACGAACTGTATGATTTAGACGTGACGGCCCCCGAAGATCCCAACGA
    -----------------------------E1a----------------------------

481 GGAGGCGGTTTCGCAGATTTTTCCCGACTCTGTAATGTTGGCGGTGCAGGAAGGGATTGA
    -----------------------------E1a----------------------------

541 CTTACTCACTTTTCCGCCGGCGCCCGGTTCTCCGGAGCCGCCTCACCTTTCCCGGCAGCC
    -----------------------------E1a----------------------------

601 CGAGCAGCCGGAGCAGAGAGCCTTGGGTCCGGTTTCTATGCCAAACCTTGTACCGGAGGT
    -----------------------------E1a----------------------------
```

Fig. 5

… # VECTOR CONSTRUCTS

This application claims the benefit of U.S. patent application Ser. No. 60/270,885, filed Feb. 23, 2001, which is herein incorporated by reference.

FIELD OF THE INVENTION

The present invention generally relates to recombinant DNA technology and the regulation of gene expression. Specifically, it relates to viral vectors that provide for controlled gene expression in the field of gene therapy.

BACKGROUND OF THE INVENTION

Gene expression in prokaryotic and eukaryotic cells is regulated on the transcriptional and translational levels. For trancription to occur, RNA synthesis is catalyzed by the enzyme RNA polymerase. Trancription starts when RNA polymerase binds to a special region, the promoter, at the start of the gene. The promoter usually precedes the first base pair that is transcribed into RNA, the startpoint. From this point, RNA polymerase moves along the template, synthesizing RNA, until it reaches the termination sequence. This action defines a transcription unit on the DNA molecule that extends from the transcription initiation site (startpoint) to the terminator.

Regulation of gene expression on the transcriptional level occurs by various mechanisms. Gene expression is controlled by particular regulatory sequences, such a promoters and enhancers, to which cellular factors may bind and thereby alter the expression rate of the adjacent gene. Such cellular factors include, for example, so-called transcription factors, which are proteins required for the recognition by RNA polymerases of specific binding sequences in genes.

Certain applications of recombinant DNA technology require that a gene be tightly regulated by its promoter, ie. that the transcription level of the gene is not dependent on any cis-acting elements other than the promoter itself. For example, in the context of gene therapy, the tissue selectivity of a viral vector administered for a therapeutical purpose may rely on the specific regulation of a gene which, therefore, should be tightly regulated by its promoter. One such gene therapy approach is directed to cancer and utilizes so-called "oncolytic adenoviral vectors." (See, for example, U.S. Pat. No. 5,998,205 (Hallenbeck et al.) Oncolytic adenoviral vectors are adenoviral vectors that are tumor-specific and replication competent after infection of the target cell in the organism. In this approach, a gene that is essential for the replication of an adenoviral vector is regulated by a tissue-specific promoter and thereby provides for tissue-specificity of the replication of the vector. Thus, in this approach, the adenoviral vectors will specifically replicate and lyse tumor cells if the gene that is essential for replication is exclusively under the control of a promoter that is tumor-specific, and is not induced by additional genetic elements that are not tissue-specific.

It is an object of the present invention to provide viral vectors, such as, for example, adenoviral vectors, that allow for the specific and tight regulation of a gene of interest within the viral vector. In the context of oncolytic adenoviral vectors, it is a further object of the present invention to provide for vectors with a high degree of tissue specificity.

BRIEF DESCRIPTION OF THE DRAWINGS

FIG. 3: Sequence of Ar6pAE2fF from left and right ends of viral DNA. Regions of Ar6pAE2fF confirmed by DNA sequencing (SEQ ID NO: 3). Panel A. Regions in first 1802 nucleotides are ITR (nucleotides 1–103), poly-adenylation signal (nucleotides 116–261), human E2F-1 promoter (nucleotides 283–555), E1a gene (nucleotides 574–1647) and a portion of the E1b gene (nucleotides 1648–1802). Panel B. Regions in the last 531 nucleotides (SEQ ID NO:4) are the PacI restriction site (nucleotides 33967–33974) (underlined), the packaging signal (nucleotides 34020–34217 and the ITR (34310–34412).

FIG. 4: Sequence of Ar6F from left end of viral DNA. The first 660 nucleotides at the left end of Ar6F (SEQ ID NO: 5). The ITR (nucleotides 1–103), a multiple cloning site (MCS) (nucleotides 104–134) and a portion of the E1a gene (nucleotides 135–660) are shown.

FIG. 5: Sequence of Ar6pAF from left end of viral DNA. The first 660 nucleotides at the left end of Ar6pAF (SEQ ID NO: 6). The ITR (nucleotides 1–103), the SV40 early polyA signal (nucleotides 104–134) and a portion of the E1a gene (nucleotides 298–660) are shown.

SUMMARY OF THE INVENTION

Figure 1:
FIG. 1: Cleavage and polyadenylation process for the SV40 early poly(A) site (SEQ ID NO:1).

The present invention provides novel viral vectors that exhibit improved regulation of one or more genes within the viral vector. In such vectors, transcription is tightly controlled by its promoter and is essentially independent of interfering genetic elements, such as, for example, cis-acting elements located in the viral vector construct itself.

Accordingly, in one aspect, the present invention provides a viral vector, which has at least one interfering genetic element, comprising at least one transcription unit, wherein at least one insulating sequence is located 5' to the transcription initiation site of said transcription unit and 3' to said interfering genetic element.

In another aspect of the invention a viral vector particle comprising the viral vector of the invention is provided.

In a further aspect of the invention, a eukaryotic cell transfected with the viral vector particle of the invention is provided.

In yet another aspect of the invention, a method of reducing the transcription level of a transcription unit in a viral vector caused by an interfering genetic element is provided, comprising the steps of identifying a suitable insulating sequence and inserting said insulating sequence into said viral vector 5' to the transcription initiation site of said transcription unit.

DETAILED DESCRIPTION OF THE INVENTION

The present invention provides novel viral vectors and, in particular, novel adenoviral vectors. Such vectors may be obtained by the insertion of an insulating sequence into a viral vector, such as, for example, the insertion of a termination signal sequence upstream of the startpoint (transcription initiation site) of the transcription unit to be shielded from non-specific transcriptional read-through. The viral vectors of the invention show a reduced amount of "leaky expression" of the gene of interest as compared to viral vectors which do not include the insulating sequence.

Generally, protein expression involves the transcription of a gene into mRNA and the translation of this mRNA into a polypeptide. Depending on the context in which used, the term "expression" may refer to the production of RNA, protein or both. The present invention is primarily concerned with the process of transcription into mRNA and its regulation.

Leaky expression is gene expression which is independent of the promoter directly upstream of the gene. In the context of gene therapy, leaky gene expression may reduce the specificity of certain therapeutic approaches. For example, the delivery of a heterologous gene may be dependent on the activation of a tissue-specific promoter driving said gene in a particular cellular environment, thereby avoiding that the gene is expressed in tissues which do not produce factors that activate the tissue-specific promoter. Such an approach will be less specific if leaky expression of the heterologous gene occurs.

The present invention now provides a method to shield a transcription unit from the unwanted regulatory influence of an interfering genetic element in a viral vector.

A transcription unit within the meaning of the invention may include one or more genes. Trancription starts when RNA polymerase binds to a special region, the promoter, at the start of the gene (the startpoint or transcription initiation site). The startpoint is the first base pair that is transcribed into RNA. From this point, RNA polymerase moves along the template, synthesizing RNA, until it reaches the termination sequence. This action defines a transcription unit that extends from the transcription initiation site to the terminator. Generally, the first nucleotide in the transcript is defined as position +1 of the transcription unit. The nucleotide immediately preceding this on the corresponding DNA strand is defined as position −1.

A transcription unit may be "operably linked" to a "regulatory element". A nucleic acid sequence is "operably linked" when it is placed into a functional relationship with another nucleic acid sequence. For instance, a regulatory element is operably linked to a transcription unit if it affects the transcription of said transcription unit. Operably linked DNA sequences are typically contiguous. However, since enhancers generally function when separated from the promoter by several kilobases and intronic sequences may be of variable lengths, some nucleic acid sequences may be operably linked but not contiguous. As used herein, the term "regulatory element" refers to a genetic element which controls some aspect of the transcription of nucleic acid sequences. Examples of regulatory elements are promoters, enhancers, polyadenylation signals, termination signals, etc.

In one aspect, the present invention provides a viral vector having at least one interfering genetic element and comprising at least one transcription unit, wherein at least one insulating sequence is located 5' to the transcription initiation site of said transcription unit and 3' to said interfering genetic element.

As used herein, the term "viral vector" is used according to its art-recognized meaning. It refers to a nucleic acid vector construct which includes at least one element of viral origin and may be packaged into a viral vector particle. The viral vector particles may be utilized for the purpose of transferring DNA into cells either in vitro or in vivo. Viral vector particles that have been commonly used for the latter purpose include particles based on retroviruses (including lentiviruses), adenoviruses, parvoviruses (such as adeno-associated viruses), and herpes viruses.

The term "interfering genetic element" is to be understood in a broad sense. Interfering genetic elements may display unwanted enhancer or promoter activity in relation to a transcription unit. In particular, an interfering genetic element of the invention may have an influence on the activity of the promoter which is directly adjacent and upstream of the gene in question. Interfering genetic elements may in particular be interfering promoters or enhancers. Enhancer or promoter activity is to be understood as any activity that increases the transcription level, i.e. the detectable amount of primary RNA transcript from the transcription unit in question. Accordingly, interfering genetic elements can be assayed by measuring transcription of any downstream gene, for example, by RT-PCR or Northern detection systems.

An interfering genetic element may have a important function which should be preserved in a viral vector. For example, in the field of adenoviral vector construction, the ITRs are critical for adenoviral DNA replication. Furthermore, sequences downstream of the left ITR are necessary for proper packaging of the viral genome. Thus, when constructing viral vectors, it may not always be possible to identify and/or delete all interfering genetic elements which display enhancer or promoter activity in relation to a transcription unit.

The term "promoter" is used according to its art-recognized meaning. It is intended to mean the DNA region, usually upstream to the coding sequence of a gene, which binds RNA polymerase and directs the enzyme to the correct transcriptional start site (transcription initiation site). Promoters are located immediately upstream (5') from the start site of transcription. Promoter sequences are required for accurate and efficient initiation of transcription. A typical promoter includes an AT-rich region called a TATA box, which is typically located approximately 30 base pairs 5' from the transcription initiation site.

The term "enhancer" is used according to its art-recognized meaning. It is intended to mean a sequence found in eukaryotes and certain eukaryotic viruses which can increase transcription from a gene when located up to several kilobases from that gene. These sequences usually act as enhancers when on the 5' side (upstream) of the gene in question. However, some enhancers are active when placed on the 3' side (downstream) of the gene. In some cases, enhancer elements can activate transcription from a gene with no known promoter. Thus, enhancers increase the rate of transcription from the promoter sequence. It is predominantly the interaction between sequence-specific transcriptional factors with the promoter and enhancer sequences that enable mammalian cells to achieve tissue-specific gene expression. The presence of these transcriptional protein factors bound to the promoter and enhancers enable other components of the transcriptional machinery, including RNA polymerase, to initiate transcription with tissue-specific selectivity and accuracy.

In a preferred embodiment of the viral vector, the insulating sequence is located directly upstream of the regulatory element to be shielded from the interfering genetic element. Dependent on the size of the regulatory element, preferredly, the insulating sequence is located no more than 3000 nucleotides upstream (5') to the transcription initiation site of the transcription unit, more preferredly, no more than 500, 300 or even 200 nucleotides. However, if a minimal promoter is used, the insulating sequence may be located no more than 17 nucleotides 5' to the transcription initiation site of the transcription unit. Preferredly, the insulating sequence is located upstream of the first transcription unit from the 5' end of the viral vector. In particular, the insulating sequence may preferredly be located upstream of the first transcription unit (as seen from the 5' end of the viral vector) which encodes a gene which is essential for replication in the respective vector. For example, if the viral vector is an adenoviral vector, the insulating sequence is preferredly located upstream of the E1a transcription unit. It is to be understood that in the context of adenoviral vector the terms "5'" and "upstream" are understood to correspond to the left ITR of the adenoviral vector.

Insulating sequences are segments of DNA that serve to isolate a gene by blocking interactions between e.g. enhancers on one side of the insulating sequence from the promoters of neighboring genes. For the purposes of the present invention, the term is to be understood in a broad functional sense. The defining characteristic of an insulating sequence within the meaning of the invention is its ability to insulate or protect a defined transcription unit which is operably linked to a regulatory element from the influence of an upstream interfering genetic element when located between the interfering genetic element and the regulatory sequence of the transcription unit to be insulated. Preferredly, insulating sequences of the invention are segments of DNA that have been isolated from their genetic source. The insulating sequence sequence may then be inserted into the viral vector at a suitable position as further described herein.

In a preferred embodiment of the present invention, the insulating sequence is a termination signal sequence; particularly preferred is a polyadenylation signal sequence. Any polyadenylation signal sequence may be useful for the purposes of the present invention. However, in preferred embodiments of this invention the termination signal sequence is either the SV40 late polyadenylation signal sequence or the SV40 early polyadenylation signal sequence. Preferredly, the termination signal sequence is isolated from its genetic source and inserted into the viral vector at a suitable position as further described herein.

A termination signal sequence within the meaning of the invention may be any genetic element that causes RNA polymerase to terminate transcription. A polyadenylation signal sequence is a recognition region necessary for endonuclease cleavage of an RNA transcript that is followed by the polyadenylation consensus sequence AATAAA (nucleotides 72–76 of SEQ ID NO: 1). A polyadenylation signal sequence provides a "polyA site", i.e. a site on a RNA transcript to which adenine residues will be added by post-transcriptional polyadenylation. Polyadenylation signal sequences are useful insulating sequences for transcription units within eukaryotes and eukaryotic viruses. Generally, the polyadenylation signal sequence includes a core poly(A) signal which consists of two recognition elements flanking a cleavage-polyadenylation site (FIG. 1). Typically, an almost invariant AAUAAA hexamer (transcribed RNA of nucleotides 72–76 of SEQ ID NO: 1) lies 20 to 50 nucleotides upstream of a more variable element rich in U or GU residues. Cleavage between these two elements is usually on the 3' side of an A residue and in vitro, is mediated by a large, multicomponent protein complex. The complex includes the cleavage and polyadenylation specific factor (CPSF), which binds the AAUAAA motif; the cleavage stimulation factor (CstF), which binds the downstream U-rich element; and two additional cleavage factors (CF I and CF II) that are less well characterized. Also, the poly(A) polymerase must be present in most cases for the cleavage step as well. The choice of a suitable polyadenylation signal sequence will consider the strength of the polyadenylation signal sequence, as completion of polyadenylation process correlates with poly(A) site strength (Chao et al., Molecular and Cellular Biology, August 1999, pp5588–5600). For example, the strong SV40 late poly(A) site is committed to cleavage more rapidly than the weaker SV40 early poly(A) site. The person skilled in the art will consider to choose a stronger polyadenylation signal sequence if a more substantive reduction of nonspecific transcription is required in a particular vector construct.

The present invention also contemplates the use of silencers as insulating sequences. A "silencer" is a DNA region which inhibits transcription initiation by interfering with enhancer activity. The insulating sequence may also be the site of binding of a repressor protein.

In another preferred embodiment of this invention, the vector construct is an adenoviral vector. In an adenoviral vector, the vector construct comprises a genetic element derived from an adenovirus. In a preferred embodiment, it comprises an adenoviral 5'ITR, an adenoviral 3'ITR and an adenoviral packaging signal. The E3 region may or may not be deleted, Accordingly, in one embodiment, the adenoviral vector further comprises a deletion in the E3 region.

Figure 2:
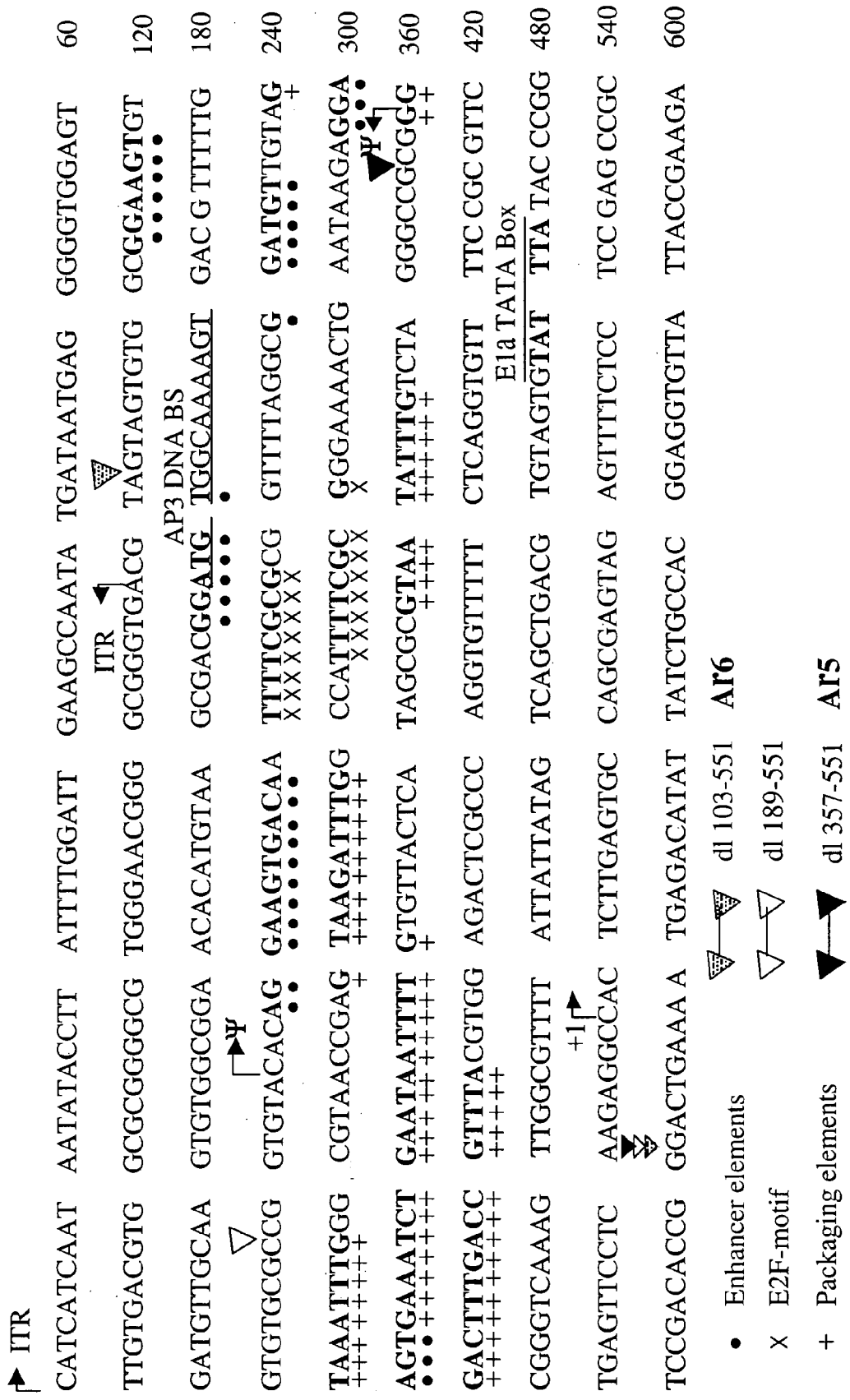
FIG. 2: E1A transcription control region (SEQ ID NO:2).

An analysis of the characteristics of the nucleotide elements around the adenoviral (Ad5) E1a region indicates that an element containing enhancer like properties lies between −141 and −305 relative to the E1a cap site at +1 (FIG. 2). This enhancer element is located very close to a sequence required in cis for packaging of viral DNA. Deletion of the enhancer element reduces both the rate of transcription and steady-state levels of E1a mRNAs in virus-infected cells. The E1a enhancer contains an 11 bp repeat element, which is a critical component of the modulatory sequence (5'-AGGAAGTGACA-3; nucleotides 199–209 of SEQ ID NO: 4. A 2–3-fold reduction of E1a expression is observed when one copy of the repeat sequence is removed, whereas expression drops 15 to 20 times when both copies are removed (Hearing and Shenk, Cell vol. 33, pp.695–303, July 1983). However, it was found that a deleted mutant can still direct the synthesis of E1a-specific mRNAs, even though it lacks the entire region from −393 to +10 relative to the E1a cap site containing the enhancer and promoters elements. It is not clear which sequences are responsible for this transcription. Accordingly, in the context of adenoviral vectors, the interfering genetic element may be located within the 5'ITR, which is a region necessary for replication of the adenovirus.

In one particular embodiment, the present invention describes a strategy to reduce nonspecific activation of the E1a gene of an adenoviral vector by blocking the read-through transcription from upstream of the E1a promoter. It is found that removal of the E1a enhancer elements (−141 to −305 relative to the E1a cap site at +1) and the insertion of a poly(A) signal sequence downstream of the left end ITR are sufficient for efficient transcription termination. An adenovirus backbone (Ar6F), with deletion from nucleotides 104 to 551, and another adenovirus backbone version, Ar6pAF, that combines the E1a deletion and the SV40 early poly(A) signal insertion upstream of the E1a gene are generated (see Example 1). In both vectors the packaging sequences are moved upstream of the right ITR. To measure read-through upstream of the E1a gene, an E1a FACS-assay is used that quantifies the levels of E1protein (see Example 2). Of the two adenoviral backbones generated, the Ar6pAF shows a reduction of E1a expression of approximately 96%. These results show that it is possible to selectively control E1a gene activity by placing the gene under the control of a tissue specific promoter, if an insulating sequence is placed immediately upstream of the promoter.

Thus, in a preferred embodiment, the adenoviral vector comprises a deletion 5' to the termination signal sequence. A deletion in the packaging signal 5' to the termination signal sequence may be such that the packaging signal becomes non-functional. In one specific embodiment, the deletion comprises a deletion 5' to the termination signal sequence wherein the deletion spans at least the nucleotides 189 to 551. In another preferred embodiment, the deletion comprises a deletion 5' to the termination signal sequence wherein the deletion spans at least nucleotides 103 to 551. In these situations, it is preferred that the packaging signal is located (i.e. re-inserted) at a position 3' to the termination signal sequence.

The viral vectors of the invention may be "replication-conditional vectors". Replication-conditional vectors are vectors which when introduced into a tissue will not replicate, or will only replicate to a minimal extent, unless a transcriptional regulatory sequence in that vector is activated or derepressed in that tissue. For example, a gene that is essential for replication may be modified by replacing the transcriptional regulatory sequence on which transcription of that gene normally depends with a heterologous transcriptional regulatory sequence. This transcriptional regulatory sequence depends upon the presence of transcriptional regulatory factors or the absence of transcriptional regulatory inhibitors. The presence of these factors in a given tissue or the absence of such inhibitors in a given tissue provides the replication-conditionality. Alternatively, the native transcriptional regulatory sequence may be disabled or rendered dysfunctional by partial removal or other mutation (one or more base changes, insertions, inversions, etc.). Replication-conditional vectors and methods for obtaining such viral vectors are further described in U.S. Pat. No. 5,998,205 (Hallenbeck et al.) which is hereby incorporated by reference in its entirety.

The term "replication" is used according to its art-recognized meaning. The essential feature is that nucleic acid copies of the original viral vector are synthesized. In the case of DNA viruses, replication at the nucleic acid level is DNA replication. In the case of RNA viruses, nucleic acid replication is replication into plus or minus strand (or both). In the case of retroviruses, replication at the nucleic acid level includes the production of cDNA as well as the further production of RNA viral genomes. Replication also includes the formation of infectious DNA or RNA viral particles. Such particles may successively infect cells in a given target tissue, thus distributing the vector through all or a significant portion of the target tissue.

In a preferred embodiment of the invention, the transcription unit to be shielded from the interfering genetic element comprises a gene essential for replication. For example, if the vector construct of the invention is an adenoviral vector, the gene essential for replication may be selected from the group consisting of the E1a, E1b, E2 and E4 coding sequences and most preferredly the gene essential for replication is selected from the group consisting of the E1a coding sequence and the E1b coding sequence. Particularly preferred is the adenoviral E1a gene as the gene essential for replication. The term "gene essential for replication" refers to a genetic sequence whose transcription is required for the vector to replicate in the target cell.

In a further embodiment of the invention, a tissue-specific transcritional regulatory sequence is operably linked to said gene essential for replication.

The term "tissue-specific" is intended to mean that the transcriptional regulatory sequence to which the gene essential for replication is operably linked functions specifically in that tissue so that replication proceeds in that tissue. This can occur by the presence in that tissue, and not in non-target tissues, of transcription factors that activate the transcriptional regulatory sequence. It can also occur by the absence of transcription inhibiting factors that normally occur in non-target tissues and prevent transcription as a result of the transcription regulatory sequence. Tissue specificity is particularly relevant in the treatment of the abnormal counterpart of a normal tissue. Such counterparts include, but are not limited to, liver tissue and liver cancer, lung tissue and lung cancer, breast tissue and breast cancer, colon tissue and colon cancer, prostate tissue and prostate cancer, and melanoma and normal skin tissue. Tissue specificity also includes the presence of an abnormal tissue type interspersed with normal tissue of a different tissue type, as for example in the case of metastases of colon cancer, breast cancer, lung cancer, prostate cancer, and the like, into tissue such as liver. In this case, the target tissue is the abnormal tissue, and tissue specificity reflects the restriction of vector replication to the abnormal tissue interspersed in the normal tissue. Tissue specificity, in the context of treatment, is particularly relevant in vivo. However, ex vivo treatment and tissue replacement also falls within the concept of tissue specificity according to the present invention.

The term "transcriptional regulatory sequence" is intended to mean any DNA sequence which can cause the linked gene to be either up- or down-regulated in a particular cell, such as for example promoter and enhancers. Various combinations of transcriptional regulatory sequences can be included in a vector. One or more may be heterologous. Further, one or more may have tissue-specificity. For example, a single transcriptional regulatory sequence could be used to drive replication by more than one gene essential for replication. This is the case, for example, when the gene product of one of the genes drives transcription of the further gene(s). An example for the case of an adenoviral vector is a heterologous promoter linked to a cassette containing an E1a coding sequence (E1a promoter deleted) and the entire E1b gene. In such a cascade, only one heterologous transcriptional regulatory sequence may be necessary. When genes are individually (separately) controlled, however, more than one transcriptional regulatory sequence can be used if more than one such gene is desired to control replication.

In a preferred embodiment the tissue-specific transcriptional regulatory sequence is a promoter or an enhancer. Preferredly, the promoter is selected from the group consisting of an E2F-responsive promoter, preferredly E2F-1, CEA, MUC1/DF3, alpha-fetoprotein, erb-B2, surfactant, tyrosinase, PSA, TK, p21, hTERT, hKLK2, probasin and cyclin gene derived promoters. The enhancer preferredly is selected from the group consisting of DF3, breast cancer-specific enhancer, PSA, viral enhancers, and steroid receptor enhancers.

The adenoviral vectors of the invention may in particular be oncolytic adenoviral vectors. Oncolytic adenoviral vectors are adenoviral vectors which selectively replicate in tumor cells and destroy the cells in which they replicate, but do not replicate to any significant degree, in non-tumor cells. For example, oncolytic adenoviral vector may have a tissue-specific transcritional regulatory sequence is operably linked to said gene essential for replication as described above. Alternatively, oncolytic adenoviral particles may include a mutation in a gene essential for adenoviral replication, such as the E1a or E1b genes. Such mutations may render adenoviral replication specific for tumor tissue, e.g. if the cells of said tissue have a defect in the p53 or Rb pathways. Oncolytic adenoviral vectors may or may not include a heterologous gene in addition to the adenoviral elements necessary for replication.

The present invention provides an oncolytic adenoviral vector, Ar6pAE2fF, that utilizes the E2F-1 promoter to drive expression of the E1a gene. The E2F-1 promoter is selectively activated in Rb pathway defective tumor cells. Transduction of A549 cells with the Ar6pAE2fF vector results in expression of E1a, indicating that this expression is dependent on the activity of the E2F-1 promoter. This result is consistent with the fact that A549 cells are defective in p16, a member of the Rb pathway. The activity of the E2F-1 promoter in Ar6pAE2fF has been also confirmed in several tumor cell lines.

In the field of cancer therapy with oncolytic adenoviral vectors, the present invention may increase the therapeutic effect because the use of an insulating sequence will reduce replication and toxicity of the oncolytic adenoviral vectors in non-target cells. Oncolytic vectors of the present invention with a polyadenylation signal inserted upstream of E1a coding region are superior to their non-modified counterparts as they demonstrated the lowest level of E1a expression (see Example 2). Thus, insertion of a polyadenylation signal sequence to stop nonspecific transcription from the left ITR will improve the specificity of E1a expression from the respective promoter. Insertion of the polyadenylation signal sequences will reduce replication of the oncolytic adenoviral vector in nontarget cells and therefore toxicity.

The present invention, in one aspect, also provides a method of reducing the transcription level of a transcription unit in a vector construct caused by an interfering genetic element that displays enhancer or promoter activity in relation to said transcription unit, comprising the steps of identifying a suitable insulating sequence and inserting said insulating sequence into said vector construct 5' to said transcription unit. In a preferred embodiment, the transcription level is reduced at least about 10-fold, preferredly at least about 20, 50 or 200-fold fold as compared to an equivalent dose of viral vectors not including the insulating sequence.

In a further embodiment, the present invention provides vector constructs which include a therapeutic gene. A therapeutic gene can be one that exerts its effect at the level of RNA or protein. For instance, a protein encoded by a therapeutic gene can be employed in the treatment of an inherited disease, e.g., the use of a cDNA encoding the cystic fibrosis transmembrane conductance regulator in the treatment of cystic fibrosis. Further, the protein encoded by the therapeutic gene can exert its therapeutic effect by causing cell death. For instance, expression of the protein, itself, can lead to cell death, as with expression of diphtheria toxin A, or the expression of the protein can render cells selectively sensitive to certain drugs, e.g., expression of the Herpes simplex (HSV) thymidine kinase gene renders cells sensitive to antiviral compounds, such as acyclovir, gancyclovir and FIAU (1-(2-deoxy-2-fluoro-.beta.-D-arabinofuranosil)-5-iodouracil). Alternatively, the therapeutic gene can exert its effect at the level of RNA, for instance, by encoding an antisense message or ribozyme, a protein that affects splicing or 3' processing (e.g., polyadenylation), or a protein that affects the level of expression of another gene within the cell, e.g. by mediating an altered rate of mRNA accumulation, an alteration of mRNA transport, and/or a change in post-transcriptional regulation.

DNA sequences encoding therapeutic genes which may be placed into the vector construct include, but are not limited to, DNA sequences encoding tumor necrosis factor (TNF) genes, such as TNF-α; genes encoding interferons such as interferon-α, interferon-β, and interferon-gamma; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding soluble CD4; Factor VIII; Factor IX; T-cell receptors; the LDL receptor, ApoE, ApoC,ApoAI and other genes involved in cholesterol transport and metabolism; the alpha-1 antitrypsin gene, the ornithine transcarbamylase gene, the CFTR gene, the insulin gene, negative selective markers or "suicide" genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, and antisense sequences which inhibit viral replication. The DNA sequence encoding the therapeutic gene may preferredly be selected from either GM-CSF, thymidine kinase, Nos, FasL, or sFasR (soluble Fas receptor).

The DNA sequence encoding the therapeutic agent may also be a sequence which is a part of the adenoviral genome, such as the adenoviral E1a gene. On one hand, E1a is instrumental in driving the adenoviral replication cycle, which in turn leads to cell lysis. Accordingly, E1a may be considered a DNA sequence encoding the therapeutic agent within the meaning of the invention if administered to, for example, a tumor tissue. Furthermore, such genes may provide an additional therapeutical benefit, e.g. by sensitizing the infected cell to certain agents and/or radiation.

For human patients, the therapeutic gene will generally be of human origin although genes of closely related species that exhibit high homology and biologically identical or equivalent function in humans may be used if the gene does not produce an adverse immune reaction in the recipient. A therapeutically effective amount of a nucleic acid sequence or a therapeutic gene is an amount effective at dosages and for a period of time necessary to achieve the desired result. This amount may vary according to various factors, including but not limited to sex, age, weight of a subject, and the like.

The DNA sequence encoding at least one therapeutic gene is under the control of a suitable promoter. Suitable promoters which may be employed include, but are not limited to, adenoviral promoters, such as the adenoviral major late promoter; or heterologous promoters, such as the cytomegalovirus (CMV) promoter; the Rous Sarcoma Virus (RSV) promoter; inducible promoters, such as the MMT promoter, the metallothionein promoter; heat shock promoters; the albumin promoter; and the ApoAI promoter. In a preferred embodiment, the promoter of the invention is an E2F-responsive promoter, in particular the E2F-1 promoter. In one embodiment of this invention, the E2F promoter is operatively linked to the E1a gene.

In addition to the E2F promoter, the following tumor selective promoters are preferredly contemplated in this invention: osteocalcin, L-plastin, CEA, AVP, c-myc, telomerase, skp-2, psma, cyclin A, and cdc25 promoters. It is to be understood, however, that the scope of the present invention is not to be limited to specific foreign genes or promoters. The selection of a particular promoter and enhancer depends on what cell type is to be used to express the protein of interest. Some eukaryotic promoters and enhancers have a broad host range while others are functional in a limited subset of cell types.

The viral vectors of the invention are useful for the delivery of genes to eukaryotic cells, for example, in order express the delivered genes and study their respective functions. Preferably, the cell is a mammalian cell. More preferably, the mammalian cell is a primate cell. Most preferably, the primate cell is a human cell. The viral vectors are also useful in studying cell transduction and gene expression in animal models.

The viral vectors are also useful for gene therapy. In particular, the expression of genes delivered by the viral vectors of the invention is useful to modify the properties of transfected cells in a pre-determined fashion for purposes of prophylaxis or therapy of disease.

Accordingly, in a further aspect, the present invention also provides a eukaryotic cell transfected with the vector construct of the invention. Preferably, the cell is a mammalian cell. More preferably, the mammalian cell is a primate cell. Most preferably, the primate cell is a human cell.

The term "transfection" as used herein refers to the introduction of foreign DNA into eukaryotic cells. Transfection may be accomplished by a variety of means known to the art, including calcium phosphate-DNA co-precipitation, DEAE-dextran-mediated transfection, polybrene-mediated transfection, electroporation, microinjection, liposome fusion, lipofection, protoplast fusion, biolistics and viral infection.

Cells which may be transfected/infected by the vector constructs of the invention include, but are not limited to, primary cells, such as primary nucleated blood cells, such as leukocytes, granulocytes, monocytes, macrophages, lymphocytes (including T-lymphocytes and B-lymphocytes), totipotent stem cells, and tumor infiltrating lymphocytes (TIL cells); bone marrow cells; endothelial cells; including activated endothelial cells; epithelial cells; keratinocytes; stem cells; hepatocytes, including hepatocyte precursor cells; fibroblasts; mesenchymal cells; mesothelial cells; parenchymal cells; vascular smooth muscle cells; brain cells and other neural cells; gut enterocytes; gut stem cells; and myoblasts. Cells which may be infected further include primary and metastatic cancer cells, including, but not limited to prostate, breast, pancreatic, lung, including both small cell and non-small cell lung cancers, colon, and liver cancers.

A cell can be present as a single entity, or can be part of a larger collection of cells. Such a "larger collection of cells" can comprise, for instance, a cell culture (either mixed or pure), a tissue, e.g., epithelial or other tissue such as a neoplastic (benign or malign) tissue, an organ (e.g., heart, lung, liver and other organs), an organ system (e.g., circulatory system, respiratory system, gastrointestinal system, or other organ system), or an organism (e.g., a bird, mammal, or the like). In one embodiment, the cells being targeted are of the circulatory system (e.g., including, but not limited to heart, blood vessels, and blood), respiratory system (e.g., nose, pharynx, larynx, trachea, bronchi, bronchioles, lungs, and the like) or the gastrointestinal system (e.g., including mouth, pharynx, esophagus, stomach, intestines, salivary glands, pancreas, liver, gallbladder, and others). In a preferred embodiment cells of neoplastic tissue (i.e. 'tumor tissue') are targeted with the targeting molecule/adenoviral particle complex of the invention.

EXAMPLES

The invention will now be described with respect to the following examples; it is to be understood, however, that the scope of the present invention is not intended to be limited thereby.

Example 1

Construction and Molecular Characterization of Replication-selective Adenoviruses Ar6F, Ar6pAF and Ar6pAE2fF Two adenovirus backbones that were expected to minimize nonspecific activation of the E1a gene were developed. The Ar6F adenoviral vector contains the left side ITR directly linked to the E1a coding region, with the intervening nucleotides deleted (nucleotides 104–551 in the Ad5 sequence, GenBank accession number M73260) and replaced with a multiple cloning site (FIG. 4; SEQ ID NO: 8). The Ar6pAF adenoviral vector is identical to Ar6F except that it contains the 145 nucleotide SV-40 early poly(A) signal inserted between the left ITR and the E1a coding region (FIG. 5; SEQ ID NO:9). In both of these vectors, the packaging signal normally present near the left ITR was moved to the right ITR (FIG. 3, panel B; SEQ ID NO: 7). This was performed by replacing the right ITR with the reverse complementary sequence of the first 392 bp of Ad5, which contains the left ITR and the packaging signal. Finally, to generate the adenoviral vector Ar6pAE2fF tumor selective promoter E2F-1 was inserted between the SV-40 early poly(A) signal and the E1a coding region present in Ar6pAF (FIG. 3, panel A; SEQ ID NO:6).

The first 1802 nucleotides of the Ar6pAE2fF adenoviral vector, including the ITR, poly(A), E2F-1 promoter and the E1a gene was confirmed by DNA sequencing (SEQ ID NO:3). In addition, the last 531 nucleotides at the right end of the vector, containing the packaging signal and right ITR was confirmed by sequencing (FIG. 3; SEQ ID NO:4).

Adenoviral genomes containing these modifications were cloned by standard methods in bacterial plasmids. Homologous recombination in *E. coli* was performed between these bacterial shuttle plasmids containing fragments of the Ad genome to generate plasmids containing full-length infectious viral genomes (He et al., 1998. A simplified system for generating recombinant adenoviruses. PNAS 95, 2509–2514). These plasmids containing full length adenoviral genomes were linearized with a restriction enzyme to release the adenoviral genome DNA from the bacterial plasmid sequences. The adenoviral DNA was then transfected into a complementing cell line AE1-2a (Gorziglia et al., 1996. Elimination of both E1 and E2a from adenovirus vectors further improves prospects for in vivo human gene therapy. J. Virol 6,4173–4178) using the LipofectaAMINE-PLUS reagent system (Life Technologies, Rockville, Md.). The cells were incubated at 37° C. for approximately 5–7 days. Adenovirus was amplified and purified by CsCl gradient as described (Jakubczak et al., 2001 Adenovirus type 5 viral particles pseudotyped with mutagenized fiber proteins show diminished infectivity of coxsackie B-Adenovirus receptor-bearing cells. J. Virol. 75:2972–2981). Virus particle concentrations were determined by spectrophotometric analysis (Mittereder et al., 1996. Evaluation of the concentration and bioactivity of adenovirus vectors for gene therapy. J Virol 70, 7498–7509).

1.2 Viral DNA Isolation and Southern Analysis

DNA was isolated from CsCl-purified virus preparation as described (Puregene Kit, Gentra). Viral DNA was digested with the indicated restriction enzymes and analyzed on 1% agarose/TAE gels containing ethidium bromide. A total of 1 ug of each DNA sample was digested with ClaI, XbaI, HpaI, SalI and BamHI and subjected to Southern analysis according to standard procedures. The probe was prepared by random oligonucleotide priming and contained the E2F-1 promoter.

Figure 6:
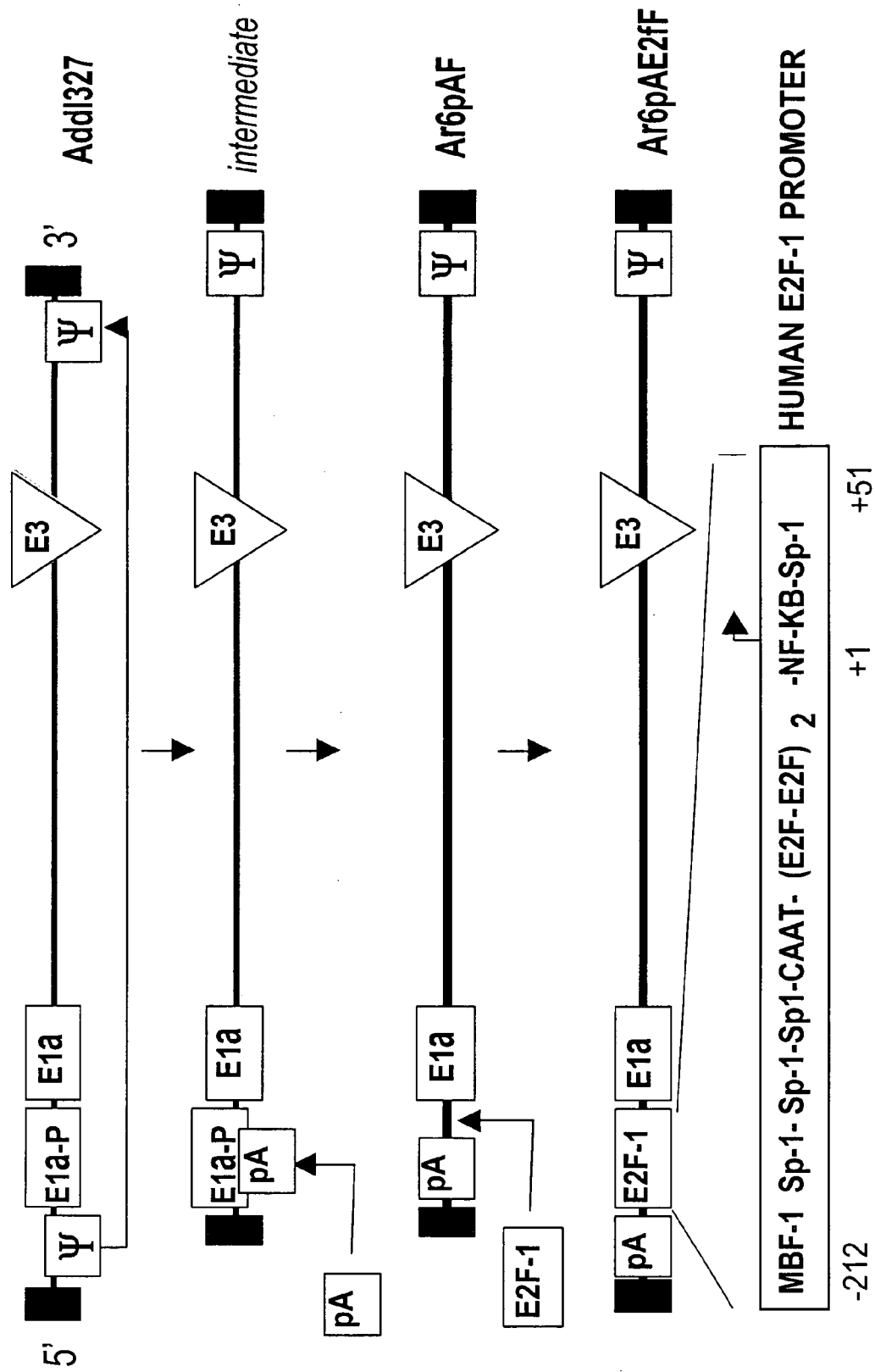
FIG. 6: Schematic diagram of Ar6pAF and Ar6pAE2fF vectors. The backbone adenoviral sequences are derived from the pAr6pAF and pAr6pAE2fF infectious plasmids. The intermediate vector backbone adenoviral sequences are derived from Addl327, an E3-detected adenovirus type 5, in which the packaging signal is located immediately upstream of the right ITR. The Ar6pAF vector backbone is deleted in the E1a promoter, and the SV-40 poly(A) signal is inserted after the left ITR. The Ar6pAE2fF vector backbone contains, after the SV-40 poly(A) signal sequences, the E2F-1 promoter (bp-212 to +51), a DNA segment of four intact E2F, one NF-kB and four Sp 1 consensus sequences.

FIG. 6 summarizes the cloning and structures of Ar6pAF and Ar6pAE2fF vectors. The DNA structure of a research lot of Ar6pAE2fF vector was confirmed by Southern analysis. The expected left DNA region fragments were obtained using five independent restriction endonucleases. Southern blot analysis with an E2F promoter DNA probe demonstrated the expected hybridization pattern for all restriction endonucleases. Thus, these results confirmed the presence of the E2F-1 promoter in the correct position and verified the integrity of the viral DNA.

1.3 Limiting Dilution Cloning of Ar6pAE2fF Vector in PER.C6 Cells

A seed lot of Ar6pAE2fF vector was produced for further evaluations. To obtain a pure seed lot of a virus it is necessary to isolate a clone derived from a single virus particle. The cloning of Ar6pAE2fF virus was accomplished through viral limiting dilution as described in below.

Ten 96 well plates of PER.C6 cells (Fallaux et al., 1998. New helper cells and matched early region 1-deleted adenovirus vectors prevent generation of replication-competent adenoviruses. Human. Gene Ther 9, 1909–1917) were plated at 5×103 cells/well in 0.04 ml volume/well. PER.C6 cells were grown in DMEM with the addition of 10% FBS and 10 mM MgCl2. 10 ul of Ar6pAE2fF containing 1×10-2 particles/ul was added to each well, giving a final infection of 0.1 particle/well. Infected cells were incubated at 37° C. and 5% CO2 for 4 hours, after which 150 ul of media was added. The virus infected cells were incubated at 37° C. and 5% CO2 for 12 days followed by scoring for CPE. The 0.1 particle/cells clones 7–9 from PER.C6 cells were harvested on day 13.Three clones, 7–9 showed CPE and were freeze thawed 5 times and amplified on PER.C6 cells plated in 6 well dishes. On day 3, CVL were prepared from clones 7–9 and clone 7 was further amplified in a T150 of PER.C6 cells. Ar6pAE2fF clone 7 T150 was harvested 2 days postinfection, a time at which the cells had reached complete CPE. The CVL was freeze thawed 5 times and cellular debris was spun out. A T75 flask of PER.C6 cells was plated and infected with 0.5 ml of the above CVL.

Of the 960 wells infected with 0.1 particle/cell, three wells showed CPE. These 3 clones were in the range of the theoretical numbers of clones expected. Statistically, only 4 wells out of the 10 plates should give CPE. This gives odds of 1:2500 that there will be more than one infectious particle/well when assuming a particle:pfu ratio of 25. The three clones were amplified in PER.C6 cells and the genome of clone 7 showed the expected size DNA fragments when analyzed with HpaI, XhoI and XbaI restriction endonuclease.

1.4 Sequence Analysis.

The 5'-end first 1802 nucleotides and the last 3'-end nucleotides from bp 33881–34412 of the plasmids pDL6pAE2f and Ar6pAE2fF clone 7 were directly sequenced.

```
Regions in Accessionary Seed lot confirmed by DNA Sequencing

1 CATCATCAATAATATACCTTATTTTGGATTGAAGCCAATATGATAATGAGGGGGTGGAGT
    +-------------------------ITR-----------------------------

61 TTGTGACGTGGCGCGGGGCGTGGGAACGGGGCGGGTGACGTAGGGCGCGATCAAGCTTAT
    +-------------------------ITR------------+              +----

121 CGATACCGTCGAAACTTGTTTATTGCAGCTTATAATGGTTACAAATAAAGCAATAGCATC
    ----------------------------polyA--------------------------

181 ACAAATTTCACAAATAAAGCATTTTTTTCACTGCATTCTAGTTGTGGTTTGTCCAAACTC
    ----------------------------polyA--------------------------

241 ATCAATGTATCTTATCATGTCTGGATCCGCGCCGCTAGCGATCATCCGGACAAAGCCTGC
    --------------------+                    +-----------------

301 GCGCGCCCCGCCCCGCCATTGGCCGTACCGCCCCGCGCCGCCGCCCCATCTCGCCCCTCG
    -----------------------E2F-1 promoter----------------------

361 CCGCCGGGTCCGGCGCGTTAAAGCCAATAGGAACCGCCGCCGTTGTTCCCGTCACGGCCG
    -----------------------E2F-1 promoter----------------------

421 GGGCAGCCAATTGTGGCGGCGCTCGGCGGCTCGTGGCTCTTTCGCGGCAAAAAGGATTTG
    -----------------------E2f-1 promoter----------------------

481 GCGCGTAAAAGTGGCCGGGACTTTGCAGGCAGCGGCGGCCGGGGCGGAGCGGGATCGAG
    -----------------------E2f-1 promoter----------------------
```

-continued

Regions in Accessionary Seed lot confirmed by DNA Sequencing

```
 541 CCCTCGATGATATCAGATCATCGGATCCCGGTCGACTGAAAATGAGACATATTATCTGCC
     ---------------+               +--------------------------

601 ACGGAGGTGTTATTACCGAAGAAATGGCCGCCAGTCTTTTGGACCAGCTGATCGAAGAGG
     ------------------------E1a gene---------------------------

661 TACTGGCTGATAATCTTCCACCTCCTAGCCATTTTGAACCACCTACCCTTCACGAACTGT
     ------------------------E1a gene---------------------------

721 ATGATTTAGACGTGACGGCCCCCGAAGATCCCAACGAGGAGGCGGTTTCGCAGATTTTTC
     ------------------------E1a gene---------------------------

781 CCGACTCTGTAATGTTGGCGGTGCAGGAAGGGATTGACTTACTCACTTTTCCGCCGGCGC
     ------------------------E1a gene---------------------------

841 CCGGTTCTCCGGAGCCGCCTCACCTTTCCCGGCAGCCCGAGCAGCCGGAGCAGAGAGCCT
     ------------------------E1a gene---------------------------

901 TGGGTCCGGTTTCTATGCCAAACCTTGTACCGGAGGTGATCGATCTTACCTGCCACGAGG
     ------------------------E1a gene---------------------------

961 CTGGCTTTCCACCCAGTGACGACGAGGATGAAGAGGGTGAGGAGTTTGTGTTAGATTATG
     ------------------------E1a gene---------------------------

1021 TGGAGCACCCCGGGCACGGTTGCAGGTCTTGTCATTATCACCGGAGGAATACGGGGGACC
     ------------------------E1a gene---------------------------

1081 CAGATATTATGTGTTCGCTTTGCTATATGAGGACCTGTGGCATGTTTGTCTACAGTAAGT
     ------------------------E1a gene---------------------------

1141 GAAAATTATGGGCAGTGGGTGATAGAGTGGTGGGTTTGGTGTGGTAATTTTTTTTTTAAT
     ------------------------E1a gene---------------------------

1201 TTTTACAGTTTTGTGGTTTAAAGAATTTTGTATTGTGATTTTTTTAAAAGGTCCTGTGTC
     ------------------------E1a gene---------------------------

1261 TGAACCTGAGCCTGAGCCCGAGCCAGAACCGGAGCCTGCAAGACCTACCCGCCGTCCTAA
     ------------------------E1a gene---------------------------

1321 AATGGCGCCTGCTATCCTGAGACGCCCGACATCACCTGTGTCTAGAGAATGCAATAGTAG
     ------------------------E1a gene---------------------------

1381 TACGGATAGCTGTGACTCCGGTCCTTCTAACACACCTCCTGAGATACACCCGGTGGTCCC
     ------------------------E1a gene---------------------------

1441 GCTGTGCCCCATTAAACCAGTTGCCGTGAGAGTTGGTGGGCGTCGCCAGGCTGTGGAATG
     ------------------------E1a gene---------------------------

1501 TATCGAGGACTTGCTTAACGAGCCTGGGCAACCTTTGGACTTGAGCTGTAAACGCCCCAG
     ------------------------E1a gene---------------------------

1561 GCCATAAGGTGTAAACCTGTGATTGCGTGTGTGGTTAACGCCTTTGTTTGCTGAATGAGT
     ------------------------E1a gene---------------------------

1621 TGATGTAAGTTTAATAAAGGGTGAGATAATGTTTAACTTGCATGGCGTGTTAAATGGGGC
     ------------------------+----------------------------------

1681 GGGGCTTAAAGGGTATATAATGCGCCGTGGGCTAATCTTGGTTACATCTGACCTCATGGA
     ------------------------E1b gene---------------------------

1741 GGCTTGGGAGTGTTTGGAAGATTTTCTGCTGTGCGTAACTTGCTGGAACAGAGCTCTAA
     ------------------------E1b gene---------------------------

1801 CA
     --

33881 AACCTACGCCCAGAAACGAAAGCCAAAAAACCCACAACTTCCTCAAATCGTCACTTCCGT

33941 TTTCCCACGTTACGTCACTTCCCATTTTAATTAAGAATTCTACAATTCCCAACACATACA

34001 AGTTACTCCGCCCTAAAACCCTGGGCGAGTCTCCACGTAAACGGTCAAAGTCCCCGCGGC
                           +-packaging signal----------------------

34061 CCTAGACAAATATTACGCGCTATGAGTAACACAAAATTATTCAGATTTCACTTCCTCTTA
     -----------------------packaging signal----------------------
```

-continued

```
Regions in Accessionary Seed lot confirmed by DNA Sequencing

34121 TTCAGTTTTCCCGCGAAAATGGCCAAATCTTACTCGGTTACGCCCAAATTTACTACAACA
      ---------------------packaging signal-----------------------

34181 TCCGCCTAAAACCGCGCGAAAATTGTCACTTCCTGTGTACACCGGCGCACACCAAAAACG
      ------------------------------------+

34241 TCACTTTTGCCACATCCGTCGCTTACATGTGTTCCGCCACACTTGCAACATCACACTTCC

34301 GCCACACTACTACGTCACCCGCCCCGTTCCCACGCCCCGCGCCACGTCACAAACTCCACC
      +------------------ITR-----------------------------

34361 CCCTCATTATCATATTGGCTTCAATCCAAAATAAGGTATATTATTGATGATG
      ---------------------------ITR---------------------+
```

Regions of Ar6pAE2fF from seedlot #TCA 254 confirmed by DNA sequencing. Regions in first 1802 nucleotides are ITR (nucleotides 1–103), poly-adenylation signal (nucleotides 116–261), human E2F-1 promoter (nucleotides 283–555), E1a gene (nucleotides 574–1647) and a portion of the E1b gene (nucleotides 1648–1802) are indicated. Regions in the last 531 nucleotides are the PacI restriction site (nucleotides 33967–33974) (underlined), the packaging signal (nucleotides 34020–34217 and the ITR (34310–34412).

Example 2

Characterization of E1a Expression by FACS

To determine if deletions of enhancer elements and insertion of a polyA signal may be sufficient for efficient transcription termination, a quantitative E1a FACS assay was used to evaluate E1a expression in a non-complementing A549 cell background (p16–p53+Rb+).

We compared the E1a expression from cells infected with Addl327, Addl312, Ar6F, Ar6pAF or Ar6pAE2fF at doses of 10, 50, 250 and 1250 virus particles per cell (VPC) (Table 1). The highest level of E1a expression was observed with the Addl327 at all range of doses. In contrast, as expected the E1a deleted mutant Addl312 showed no E1a expression. Under the conditions used in this experiment (10 to 1250 VPC) there was about 80% to 22% less E1a detected in cells transduced with Ar6F than in those transduced with Addl327. The E1a expression in cells transduced with Ar6pAF was significantly reduced about 100% to 96%, in all doses, as compared to the expression from cells infected with the Addl327. The expression of E1a from cells infected with the Ar6pAE2fF oncolytic vector was reduced 50% as compared with the Addl327 virus at a dose of 50VPC.

In conclusion, the insertion of a poly(A) signal in the Ar6pAF vector reduced the E1a expression in A549 cells. In contrast, insertion of the E2F-1 promoter reestablished the E1a expression, thus demonstrating that E1a expression was exclusively due to the inserted promoter.

TABLE 1

E1a expression in A549 noncomplementing cells.
Noncomplementing A549 cells were infected with either
vector at 10, 50, 250 and 1250 VPC. E1a expression was
determined 24 hours postinfection by FACS.

|          | 10 vpc      | 50 vpc      | 250 vpc     | 1250 vpc    |
|----------|-------------|-------------|-------------|-------------|
| AddI327  | 27.5 ± 2.2  | 72.9 ± 3.8  | 94.4 ± 0.7  | 98.4 ± 0.4  |
| AddI312  | 0.0 ± 0.0   | 0.0 ± 0.0   | 0.0 ± 0.0   | 0.0 ± 0.0   |
| Ar6F     | 5.6 ± 0.8   | 28.3 ± 1.1  | 59.4 ± 4.7  | 76.9 ± 3.6  |
| Ar6pAF   | 0.0 ± 0.0   | 0.1 ± 0.1   | 0.3 ± 0.1   | 3.8 ± 2.4   |
| Ar6pAE2fF| ND          | 39.7 ± 0.1  | ND          | ND          |

Protocol for E1a FACS Assays

Cells were plated the day before infection in 12-well plates. The next day, media was aspirated from cells, virus dose formulations in particles per cell were added to the wells and the plates were rocked at 37° C. for 4 hours. Virus/media was aspirated, washed one time, then replaced with complete growth media and incubated 20 hours at 37° C. Cells were harvested by trypsin-EDTA digestion, and fixed in 70% ethanol for 20 minutes at room temperature. Then the cells were washed one time and resuspended in FACS buffer (PBS, 3% FBS, 0.1% NaN$_3$). 10 µl of a 1:10 dilution of unconjugated anti-E1a antibody (Calbiochem, Anti-Adenovirus 2E1A, Human (Ab-1)) or mouse IgG$_2$a isotype control (Sigma M-5409) was added and incubated at room temperature for 30 minutes. The cells were washed one time with FACS buffer. Then 50µl of 1:40 dilution of GAM PE (Sigma P-9670) was added and incubated at room temperature for 30 minutes. Then the cells were washed, resuspended in 200 µl FACS buffer, and 20,000 events on FACSCAN were acquired.

Example 3

Toxicity of Adenoviral Vectors

Acute hepatic toxicity in Balb/c SCID male mice is used to distinguish between adenoviral vectors with different levels of E1a activity. A profound difference in serum liver enzyme elevations is observed between vectors with wild-type E1a expression and those with minimal or silent E1a expression.

Studies were designed with ten animals per group. Control groups were HBSS vehicle alone, the negative control E1a-deleted Addl312 and the E1a-containing positive control Addl327. Viruses were injected at a dose of $6.25 \times 10^{11}$ particles/kg intravenously into the tail vein in a volume of 10 ml/kg; an equivalent dose volume of HBSS (10 mL/kg) was injected in the vehicle control group. Animals were injected on study day 1, with an interim sacrifice of half of each group on study day 4 and a terminal sacrifice of the remaining animals on study day 15. On study days 4 and 15, serum was collected from all mice, and the livers removed from the animals scheduled for sacrifice (5/group). In addition, body weights were measured on all surviving mice on study days −3, 1, 3, 4, 8 and 15.

Figure 7:
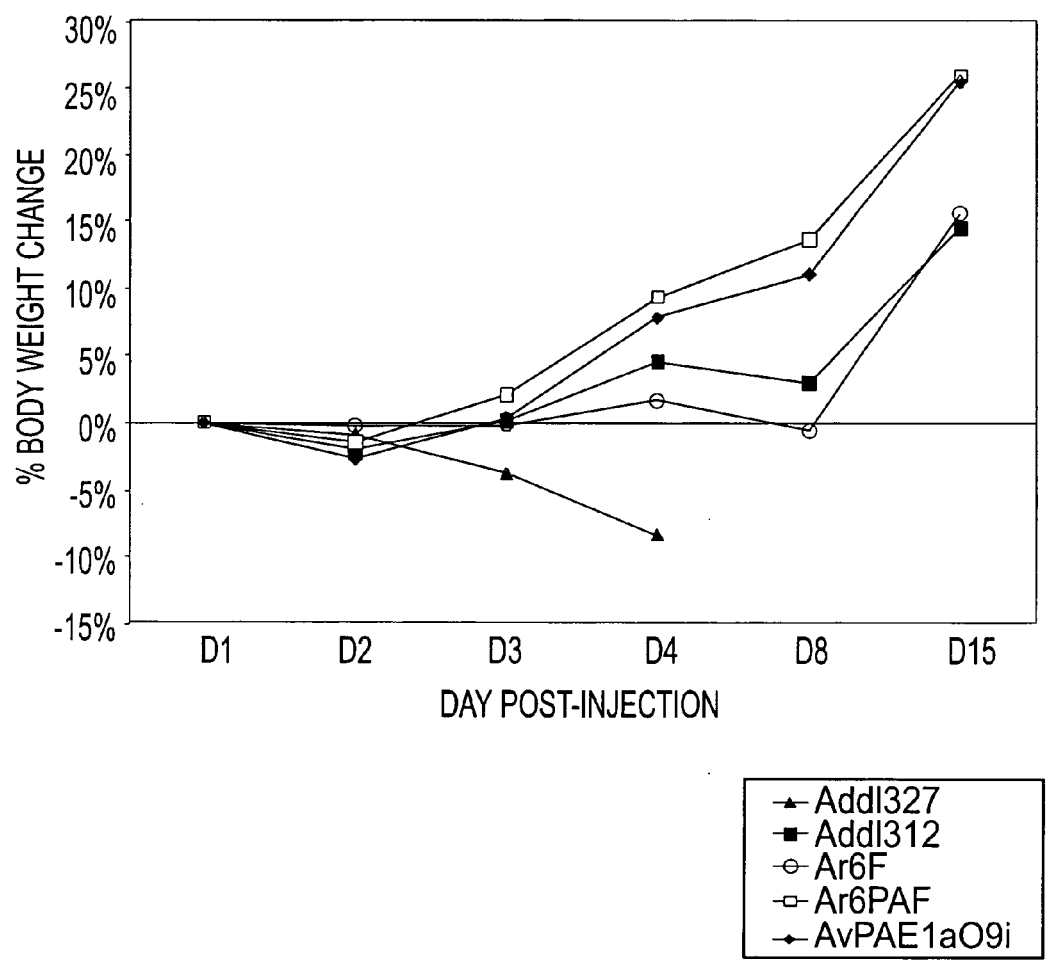
FIG. 7: Comparison of body weight change after administration of vectors Addl327, AvE1aPA09lxl, Ar6F, Ar6pAF, Addl312.
Figure 8:
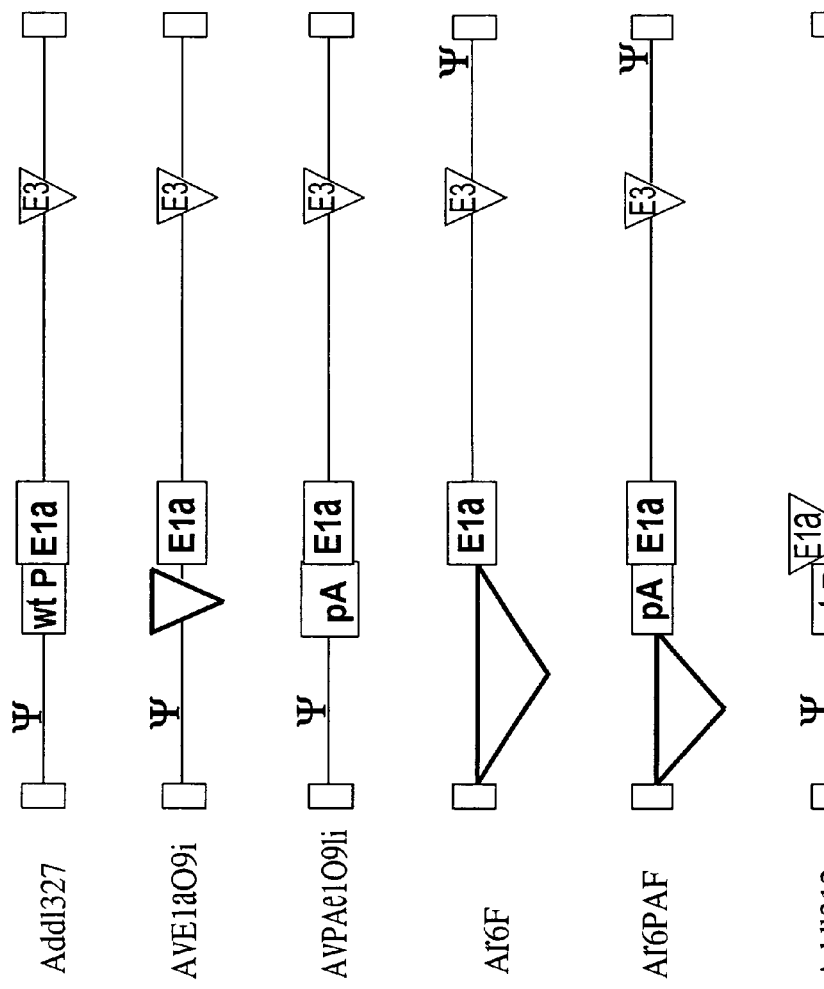
FIG. 8: Backbones of vectors Addl327, AvE1a09i, AvPAE1a09i, Ar6F, Ar6pAF, Addl312.

The acute toxicity of E1a-containing adenoviral vectors in the backbones Ar6F, Ar6PAF was compared. Viruses are prepared as described in Example 1. Based on body weight change (FIG. 7, map of constructs see FIG. 8) and serum ALT and AST levels (Table 2), the hepatotoxicity of Ar6F was higher than Ar6pAF.

TABLE 2

| Vector | ALT | | AST | | DB | |
|---|---|---|---|---|---|---|
| | mean | sd | mean | sd | mean | sd |
| Ar6F | 2213.40 | 1018.61 | 1500.40 | 922.53 | 0.19 | 0.33 |
| Ar6pAF | 57.6* | 24.59 | 130.7* | 40.33 | 0.01* | 0.03 |

*significant difference versus Ar6F ($p < 0.05$)

The disclosures of all patents, publications (including published patent applications), and database accession numbers referred to in this specification are specifically incorporated herein by reference in their entirety to the same extent as if each such individual patent, publication and database number were specifically and individually indicated to be incorporated by reference in its entirety.

SEQUENCE LISTING

<160> NUMBER OF SEQ ID NOS: 8

<210> SEQ ID NO 1
<211> LENGTH: 140
<212> TYPE: DNA
<213> ORGANISM: Simian virus 40
<220> FEATURE:
<221> NAME/KEY: misc_feature
<222> LOCATION: (1)..(140)
<223> OTHER INFORMATION: Fig. 1 A

<400> SEQUENCE: 1

```
cttatcgata ccgtcgaaac ttgtttattg cagcttataa tggttacaaa taaagcaaca      60
caaatttcac aaataaagca ttttttttcac tgcattctag ttgtggtttg tccaaactca     120
tcaatgtatc ttatcatgtc                                                 140
```

<210> SEQ ID NO 2
<211> LENGTH: 600
<212> TYPE: DNA
<213> ORGANISM: Human adenovirus type 5
<220> FEATURE:
<221> NAME/KEY: misc_feature
<222> LOCATION: (1)..(600)
<223> OTHER INFORMATION: Fig. 2 - E1A transcription control region

<400> SEQUENCE: 2

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg tgtagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
```

<210> SEQ ID NO 3
<211> LENGTH: 1802
<212> TYPE: DNA
<213> ORGANISM: Artificial Sequence
<220> FEATURE:
<223> OTHER INFORMATION: viral vector construct
<220> FEATURE:
<221> NAME/KEY: misc_feature
<222> LOCATION: (1)..(1802)
<223> OTHER INFORMATION: Fig. 3 A - left end of Ar6pAE2fF sequence

<400> SEQUENCE: 3

```
catcatcaat aatataccct attttggatt gaagccaata tgataatgag ggggtggagt        60
ttgtgacgtg gcgcggggcg tgggaacggg gcgggtgacg tagggcgcga tcaagcttat       120
cgataccgtc gaaacttgtt tattgcagct tataatggtt acaaataaag caatagcatc       180
acaaatttca caaataaagc attttttca ctgcattcta gttgtggttt gtccaaactc        240
atcaatgtat cttatcatgt ctggatccgc gccgctagcg atcatccgga caaagcctgc       300
gcgcgcccg ccccgccatt ggccgtaccg ccccgcgccg ccgccccatc tcgcccctcg        360
ccgccgggtc cggcgcgtta agccaatag gaaccgccgc cgttgttccc gtcacggccg        420
gggcagccaa ttgtggcggc gctcggcggc tcgtggctct ttcgcggcaa aaaggatttg       480
gcgcgtaaaa gtggccggga cttttgcaggc agcggcggcc ggggcggag cgggatcgag       540
ccctcgatga tatcagatca tcggatcccg gtcgactgaa aatgagacat attatctgcc      600
acggaggtgt tattaccgaa gaaatggccg ccagtctttt ggaccagctg atcgaagagg      660
tactggctga taatcttcca cctcctagcc attttgaacc acctacccct cacgaactgt      720
atgatttaga cgtgacggcc cccgaagatc ccaacgagga ggcggtttcg cagattttc      780
ccgactctgt aatgttggcg gtgcaggaag ggattgactt actcacttt ccgccggcgc      840
ccggttctcc ggagccgcct caccctttccc ggcagcccga gcagccggag cagagagcct    900
tgggtccggt ttctatgcca aaccttgtac cggaggtgat cgatcttacc tgccacgagg      960
ctggctttcc acccagtgac gacgaggatg aagagggtga ggagtttgtg ttagatattg     1020
tggagcaccc cggggcacggt tgcaggtctt gtcattatca ccggaggaat acggggggacc    1080
cagatattat gtgttcgctt tgctatatga ggacctgtgg catgtttgtc tacagtaagt     1140
gaaaattatg ggcagtgggt gatagagtgg tgggtttggt gtggtaattt ttttttttaat    1200
ttttacagtt ttgtggttta aagaattttg tattgtgatt ttttttaaaag gtcctgtgtc    1260
tgaacctgag cctgagcccg agccagaacc ggagcctgca agacctaccc gccgtcctaa     1320
aatggcgcct gctatcctga gacgcccgac atcacctgtg tctagagaat gcaatagtag    1380
tacggatagc tgtgactccg gtccttctaa cacacctcct gagatacacc cggtggtccc    1440
gctgtgcccc attaaaccag ttgccgtgag agttggtggg cgtcgccagg ctgtggaatg    1500
tatcgaggac ttgcttaacg agcctgggca acctttggac ttgagctgta acgccccag    1560
gccataaggt gtaaacctgt gattgcgtgt gtggttaacg cctttgtttg ctgaatgagt   1620
tgatgtaagt ttaataaagg gtgagataat gtttaacttg catggcgtgt taaatggggc    1680
ggggcttaaa gggtatataa tgcgccgtgg gctaatcttg gttacatctg acctcatgga    1740
ggcttgggag tgtttggaag atttttctgc tgtgcgtaac ttgctggaac agagctctaa   1800
ca                                                                    1802
```

<210> SEQ ID NO 4

```
<211> LENGTH: 532
<212> TYPE: DNA
<213> ORGANISM: Artificial Sequence
<220> FEATURE:
<223> OTHER INFORMATION: viral vector construct
<220> FEATURE:
<221> NAME/KEY: misc_feature
<222> LOCATION: (1)..(532)
<223> OTHER INFORMATION: Fig. 3 B - right end of Ar6pAE2fF sequence

<400> SEQUENCE: 4
aacctacgcc cagaaacgaa agccaaaaaa cccacaactt cctcaaatcg tcacttccgt      60
tttcccacgt tacgtcactt cccatttttaa ttaagaattc tacaattccc aacacataca    120
agttactccg ccctaaaacc ctgggcgagt ctccacgtaa acggtcaaag tccccgcggc     180
cctagacaaa tattacgcgc tatgagtaac acaaaattat tcagatttca cttcctctta    240
ttcagttttc ccgcgaaaat ggccaaatct tactcggtta cgcccaaatt tactacaaca    300
tccgcctaaa accgcgcgaa aattgtcact tcctgtgtac accggcgcac accaaaaacg    360
tcacttttgc cacatccgtc gcttacatgt gttccgccac acttgcaaca tcacacttcc    420
gccacactac tacgtcaccc gccccgttcc cacgccccgc gccacgtcac aaactccacc    480
ccctcattat catattggct tcaatccaaa ataaggtata ttattgatga tg            532

<210> SEQ ID NO 5
<211> LENGTH: 660
<212> TYPE: DNA
<213> ORGANISM: Artificial Sequence
<220> FEATURE:
<223> OTHER INFORMATION: viral vector construct
<220> FEATURE:
<221> NAME/KEY: misc_feature
<222> LOCATION: (1)..(660)
<223> OTHER INFORMATION: Fig. 4 - left end of Ar6F sequence

<400> SEQUENCE: 5
catcatcaat aatataccct attttggatt gaagccaata tgataatgag ggggtggagt      60
ttgtgacgtg gcgcggggcg tgggaacggg gcgggtgacg tagggcgcgc cgctagcgat    120
atcggatccc ggtcgactga aaatgagaca tattatctgc cacggaggtg ttattaccga    180
agaaatggcc gccagtcttt tggaccagct gatcgaagag gtactggctg ataatcttcc    240
acctcctagc cattttgaac cacctaccct tcacgaactg tatgatttag acgtgacggc    300
ccccgaagat cccaacgagg aggcggtttc gcagattttt cccgactctg taatgttggc    360
ggtgcaggaa gggattgact tactcacttt tccgccggcg cccggttctc cggagccgcc    420
tcacctttcc cggcagcccg agcagccgga gcagagagcc ttgggtccgg tttctatgcc    480
aaaccttgta ccggaggtga tcgatcttac ctgccacgag gctggctttc cacccagtga    540
cgacgaggat gaagagggtg aggagtttgt gttagattat gtggagcacc ccgggcacgg    600
ttgcaggtct tgtcattatc accggaggaa tacgggggac ccagatatta tgtgttcgct    660

<210> SEQ ID NO 6
<211> LENGTH: 660
<212> TYPE: DNA
<213> ORGANISM: Artificial Sequence
<220> FEATURE:
<223> OTHER INFORMATION: viral vector construct
<220> FEATURE:
<221> NAME/KEY: misc_feature
<222> LOCATION: (1)..(660)
<223> OTHER INFORMATION: Fig. 5 - left end of Ar6pAF sequence

<400> SEQUENCE: 6
```

```
catcatcaat aatatacctt attttggatt gaagccaata tgataatgag ggggtggagt        60
ttgtgacgtg gcgcggggcg tgggaacggg gcgggtgacg tagggcgcga tcaagcttat       120
cgataccgtc gaaacttgtt tattgcagct tataatggtt acaaataaag caatagcatc       180
acaaatttca caaataaagc attttttca  ctgcattcta gttgtggttt gtccaaactc       240
atcaatgtat cttatcatgt ctggatccgc gccgctagcg atatcggatc ccggtcgact       300
gaaaatgaga catattatct gccacggagg tgttattacc gaagaaatgg ccgccagtct       360
tttggaccag ctgatcgaag aggtactggc tgataatctt ccacctccta gccattttga       420
accacctacc cttcacgaac tgtatgattt agacgtgacg gcccccgaag atcccaacga       480
ggaggcggtt tcgcagattt ttcccgactc tgtaatgttg gcggtgcagg aagggattga       540
cttactcact tttccgccgg cgcccggttc tccggagccg cctcacctt  cccggcagcc       600 cgagcagccg gagcagagag ccttgggtcc ggtttctatg ccaaaccttg taccggaggt       660
```

<210> SEQ ID NO 7
<211> LENGTH: 11
<212> TYPE: DNA
<213> ORGANISM: Human adenovirus type 5
<220> FEATURE:
<221> NAME/KEY: misc_feature
<222> LOCATION: (1)..(11)
<223> OTHER INFORMATION: 11 bp repeat element in the E1a enhancer

<400> SEQUENCE: 7
aggaagtgac a                                                            11

<210> SEQ ID NO 8
<211> LENGTH: 24
<212> TYPE: DNA
<213> ORGANISM: Artificial Sequence
<220> FEATURE:
<223> OTHER INFORMATION: Viral vector sequence
<220> FEATURE:
<221> NAME/KEY: misc_feature
<222> LOCATION: (1)..(24)
<223> OTHER INFORMATION: Fig. 1C. SV40 early Poly(A) site
<220> FEATURE:
<221> NAME/KEY: polyA_site
<222> LOCATION: (3)..(24)
<223> OTHER INFORMATION:

<400> SEQUENCE: 8
gcaaaaaaaa aaaaaaaaaa aaaa                                              24

What is claimed is:

1. A replication conditional adenoviral vector comprising a left ITR, an E1a transcription unit and at least one insulating sequence, wherein said at least one insulating sequence is isolated from its genetic source and inserted 5' to the transcription initiation site of said E1a transcription unit and 3' to said left ITR and the adenoviral packaging signal.

2. The adenoviral vector of claim 1, wherein said insulating sequence is a termination signal sequence.

3. The adenoviral vector of claim 1, further comprising a therapeutic gene.

4. A adenoviral vector particle comprising the adenoviral vector of claim 1.

5. The adenoviral vector of claim 1, wherein the transcription unit of said adenoviral vector is operably linked to a tissue-specific transcriptional regulatory sequence and wherein said adenoviral vector selectively replicates in tumor cells.

6. The adenoviral vector of claim 2, wherein the termination signal sequence is a polyadenylation signal sequence.

7. The adenoviral vector of claim 6, wherein the polyadenylation signal sequence is the SV40late polyadenylation signal sequence.

8. The adenoviral vector of claim 6, wherein the polyadenylation signal sequence is the SV40early polyadenylation signal sequence.

9. A eukaryotic cell transfected with the adenoviral vector particle of claim 4.

10. The adenoviral vector of claim 5, wherein the sequence located between −141 and −305 relative to the E1a transcription initiation site at +1 has been removed.

11. The adenoviral vector of claim 5, wherein said tissue-specific transcriptional regulatory sequence is a promoter or an enhancer.

12. The adenoviral vector of claim 5, further comprising a deletion in the E3 region.

13. The adenoviral vector of claim 5, further comprising a therapeutic gene.

14. An adenoviral vector particle comprising the adenoviral vector of claim 5.

15. The adenoviral vector of claim 11, wherein said promoter is selected from the group consisting of E2F, CEA, MUC1/DF3, alpha-fetoprotein, erb-B2, surfactant, tyrosinase, PSA, TK, p21, hTERT, hKLK2, probasin and cyclin gene derived promoters.

16. The adenoviral vector of claim 11, wherein said enhancer is selected from the group consisting of DF3, breast cancer-specific enhancer, viral enhancers, and steroid receptor enhancers.

17. The adenoviral vector of claim 15, wherein said insulating sequence is a termination signal sequence.

18. The adenoviral vector of claim 17, wherein said termination signal sequence is a polyadenylation signal sequence.

19. The adenoviral vector of claim 18, wherein said polyadenylation signal sequence is the SV40late polyadenyiation signal sequence.

20. The adenoviral vector of claim 16, wherein said polyadenylation signal sequence is the SV40early polyadenylation signal sequence.

21. The replication conditional adenoviral vector of claim 15, wherein said promoter is an E2F promoter.

22. The replication conditional adenoviral vector of claim 15, wherein said promoter is an hTERT promoter.

23. A eukaryotic cell transfected with the adenoviral vector particle of claim 14.

24. The replication conditional adenoviral vector of claim 3, wherein said therapeutic gene is a cytokine.

25. The replication conditional adenoviral vector of claim 24, wherein said cytokine is GM-CSF.

26. The replication conditional adenoviral vector of claim 13, wherein said therapeutic gene is a cytokine.

27. The replication conditional adenoviral vector of claim 26, wherein said cytokine is GM-CSF.

* * * * *